(12) United States Patent
Hustedt

(10) Patent No.: US 12,178,425 B2
(45) Date of Patent: Dec. 31, 2024

(54) SUTURE BASED CLAMPING DEVICE

(71) Applicant: RESPONSIVE ARTHROSCOPY, LLC, Minneapolis, MN (US)

(72) Inventor: Jacob Hustedt, Sandy, UT (US)

(73) Assignee: Responsive Arthroscopy, LLC, Minneapolis, MN (US)

( * ) Notice: Subject to any disclaimer, the term of this patent is extended or adjusted under 35 U.S.C. 154(b) by 132 days.

(21) Appl. No.: 18/046,439

(22) Filed: Oct. 13, 2022

(65) Prior Publication Data

US 2023/0210516 A1 Jul. 6, 2023

Related U.S. Application Data

(63) Continuation of application No. 17/651,747, filed on Feb. 18, 2022, now Pat. No. 11,510,665, which is a continuation of application No. PCT/US2021/023101, filed on Mar. 19, 2021.

(60) Provisional application No. 63/002,272, filed on Mar. 30, 2020.

(51) Int. Cl.
 *A61B 17/04* (2006.01)
(52) U.S. Cl.
 CPC .. *A61B 17/0401* (2013.01); *A61B 2017/0404* (2013.01); *A61B 2017/044* (2013.01); *A61B 2017/0453* (2013.01); *A61B 2017/0454* (2013.01); *A61B 2017/0496* (2013.01)
(58) Field of Classification Search
 CPC ...... A61B 2017/044; A61B 2017/0453; A61B 2017/0409; A61B 2017/0404; A61B 2017/0406; A61B 2017/0417; A61B 2017/0496; A61B 2017/565; A61B 17/0401; A61B 17/8869; A61B 17/8061; A61B 17/888

See application file for complete search history.

(56) References Cited

U.S. PATENT DOCUMENTS

| | | |
|---|---|---|
| 3,845,575 A | 11/1974 | Boden |
| 3,953,144 A | 4/1976 | Boden |
| 6,185,798 B1 | 2/2001 | Ton |
| 6,585,730 B1 | 7/2003 | Foerster |
| 7,637,926 B2 | 12/2009 | Foerster et al. |
| 8,100,923 B2 | 1/2012 | Paraschac et al. |
| 8,133,258 B2 | 3/2012 | Foerster et al. |
| 8,162,978 B2 | 4/2012 | Lombardo et al. |
| 8,371,004 B2 | 2/2013 | Huber et al. |
| 8,409,252 B2 | 4/2013 | Lombardo et al. |

(Continued)

FOREIGN PATENT DOCUMENTS

| | | |
|---|---|---|
| EP | 3235471 A1 | 10/2017 |
| WO | WO-2020056029 A1 | 3/2020 |

(Continued)

OTHER PUBLICATIONS

PCT/US2019/050659 International Search Report dated Dec. 31, 2019.

(Continued)

*Primary Examiner* — Majid Jamialahmadi
(74) *Attorney, Agent, or Firm* — Goodwin Procter LLP

(57) ABSTRACT

Systems, assemblies, and methods are provided herein for fastening of one bone to another bone using one or more sutures. The features herein enable such fastening with a more accurate strength, and which can be more easily fastened in-situ.

18 Claims, 29 Drawing Sheets

(56) References Cited

U.S. PATENT DOCUMENTS

| | | |
|---|---|---|
| 8,652,173 B2 | 2/2014 | Mansmann |
| 8,790,346 B2 | 7/2014 | Daniels et al. |
| 9,168,034 B2 | 10/2015 | Lombardo et al. |
| 9,226,742 B2 | 1/2016 | Wolf et al. |
| 9,241,706 B2 | 1/2016 | Paraschac et al. |
| 9,277,910 B2 | 3/2016 | Nason et al. |
| 9,295,460 B2 | 3/2016 | Hoof et al. |
| 9,345,467 B2 | 5/2016 | Lunn et al. |
| 9,402,617 B2 | 8/2016 | Baird |
| 9,463,010 B2 | 10/2016 | Gittings et al. |
| 9,687,224 B2 | 6/2017 | Lunn et al. |
| 9,936,939 B2 | 4/2018 | Nguyen et al. |
| 10,076,377 B2 | 9/2018 | Bonutti et al. |
| 10,159,477 B2 | 12/2018 | Lunn et al. |
| 10,238,377 B2 | 3/2019 | Nason et al. |
| 11,298,120 B2 | 4/2022 | Bowman et al. |
| 11,510,665 B2 | 11/2022 | Hustedt |
| 2003/0195563 A1 | 10/2003 | Foerster |
| 2005/0119663 A1 | 6/2005 | Keyer et al. |
| 2006/0265010 A1 | 11/2006 | Paraschac et al. |
| 2006/0282119 A1 | 12/2006 | Perchik |
| 2007/0060922 A1 | 3/2007 | Dreyfuss |
| 2007/0213770 A1 | 9/2007 | Dreyfuss |
| 2007/0276437 A1 | 11/2007 | Call et al. |
| 2008/0051836 A1 | 2/2008 | Foerster et al. |
| 2008/0275469 A1 | 11/2008 | Fanton et al. |
| 2008/0294204 A1 | 11/2008 | Chirico et al. |
| 2009/0012522 A1 | 1/2009 | Lob |
| 2009/0012571 A1* | 1/2009 | Perrow .............. A61B 17/1728 606/280 |
| 2009/0292321 A1 | 11/2009 | Collette |
| 2010/0004683 A1 | 1/2010 | Hoof et al. |
| 2011/0004242 A1 | 1/2011 | Stchur |
| 2011/0166599 A1 | 7/2011 | Jervis et al. |
| 2011/0238113 A1 | 9/2011 | Fanton et al. |
| 2012/0123474 A1* | 5/2012 | Zajac .................. A61B 17/842 606/232 |
| 2013/0030479 A1 | 1/2013 | Regauer |
| 2013/0123841 A1* | 5/2013 | Lyon .................. A61B 17/0401 606/232 |
| 2013/0144334 A1 | 6/2013 | Bouduban et al. |
| 2013/0197578 A1 | 8/2013 | Gregoire et al. |
| 2014/0081323 A1 | 3/2014 | Hawkins |
| 2014/0257294 A1 | 9/2014 | Gedet et al. |
| 2014/0379028 A1 | 12/2014 | Lo |
| 2016/0030035 A1 | 2/2016 | Zajac et al. |
| 2016/0089131 A1 | 3/2016 | Wade |
| 2016/0100833 A1 | 4/2016 | Lunn et al. |
| 2016/0235398 A1 | 8/2016 | Nguyen et al. |
| 2016/0302785 A1 | 10/2016 | Nason et al. |
| 2017/0065273 A1 | 3/2017 | Hart et al. |
| 2017/0189007 A1 | 7/2017 | Burkhart et al. |
| 2018/0249998 A1* | 9/2018 | Chavan .............. A61B 17/0401 |
| 2018/0368827 A1 | 12/2018 | Balboa et al. |
| 2019/0038275 A1 | 2/2019 | Clark et al. |
| 2019/0117377 A1 | 4/2019 | Ticker |
| 2019/0167254 A1 | 6/2019 | Balboa et al. |
| 2019/0175223 A1* | 6/2019 | Nguyen .............. A61B 17/8605 |
| 2019/0343507 A1 | 11/2019 | Chavan et al. |
| 2019/0380695 A1 | 12/2019 | Fallin et al. |
| 2019/0380747 A1 | 12/2019 | Fischer et al. |
| 2020/0077999 A1 | 3/2020 | Bowman et al. |
| 2022/0054122 A1 | 2/2022 | Bowman et al. |
| 2022/0167963 A1 | 6/2022 | Hustedt |
| 2022/0192655 A1 | 6/2022 | Bowman et al. |
| 2023/0320720 A1 | 10/2023 | Bahoora et al. |
| 2023/0320721 A1 | 10/2023 | Bahoora et al. |

FOREIGN PATENT DOCUMENTS

| | | |
|---|---|---|
| WO | WO-2021202123 A1 | 10/2021 |
| WO | WO-2022039991 A1 | 2/2022 |
| WO | WO-2023044295 A1 | 3/2023 |

OTHER PUBLICATIONS

PCT/US2021/023101 International Search Report and Written Opinion mailed Jun. 24, 2021.
PCT/US2021/045506 International Search Report and Written Opinion dated Jan. 31, 2022.
U.S. Appl. No. 17/651,747, filed Feb. 18, 2022.
U.S. Appl. No. 17/654,170, filed Mar. 9, 2022.
U.S. Appl. No. 16/569,752, filed Sep. 13, 2019, U.S. Pat. No. 11,298,120, Apr. 12, 2022, Issued.
U.S. Appl. No. 17/654,170, filed Mar. 9, 2022, Pending.
U.S. Appl. No. 17/401,263, filed Aug. 12, 2021, Pending.
U.S. Appl. No. 17/651,747, filed Feb. 18, 2022, Allowed.
U.S. Appl. No. 17/651,747, filed Feb. 18, 2022, U.S. Pat. No. 11,510,665, Nov. 29, 2022, Issued.
U.S. Appl. No. 18/335,911, filed Jun. 15, 2023, Pending.
U.S. Appl. No. 18/335,914, filed Jun. 15, 2023, Pending.
PCT/US2022/076334 International Search Report and Written Opinion mailed Dec. 13, 2022.

* cited by examiner

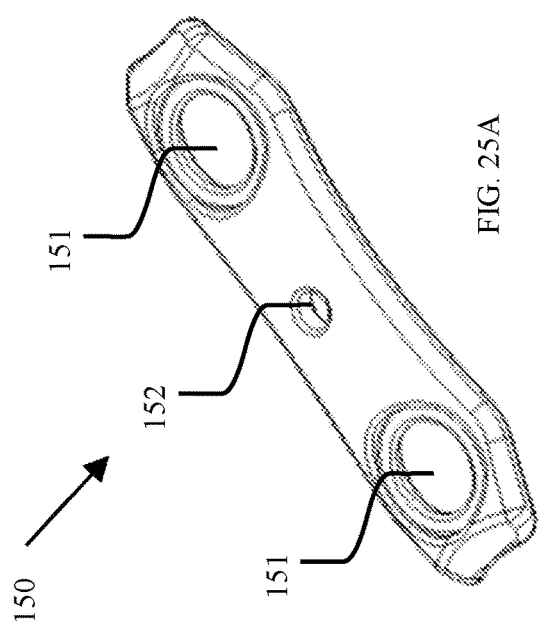
FIG. 25A
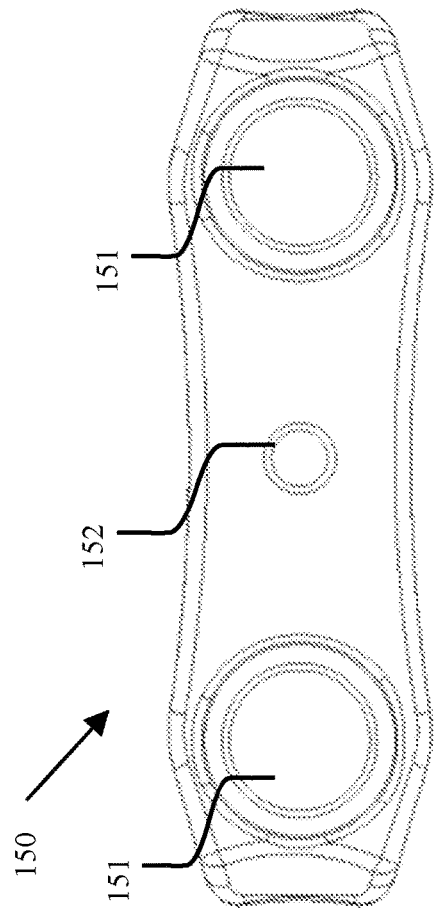
FIG. 25C
FIG. 25B

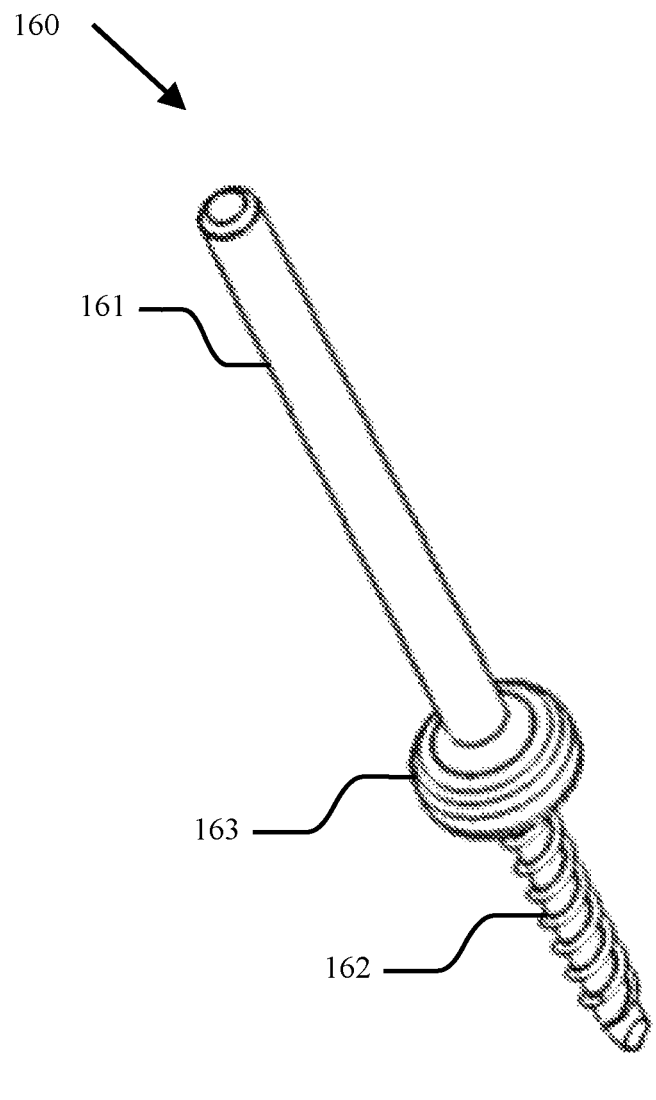
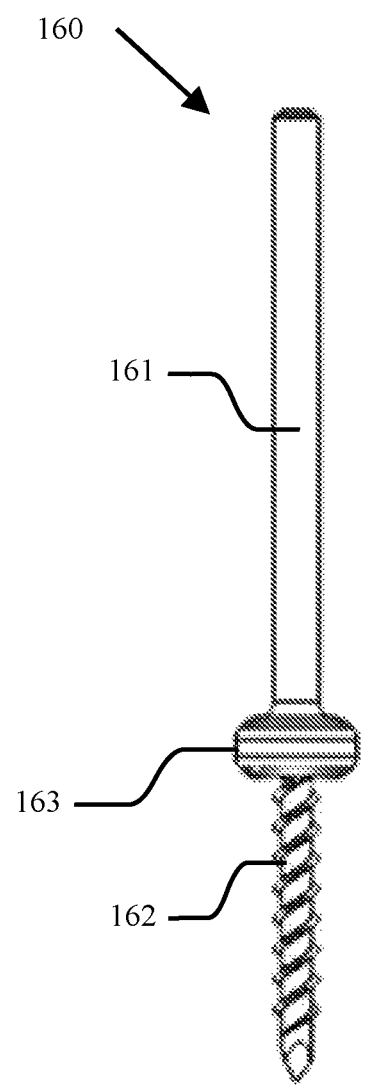
FIG. 26A
FIG. 26B

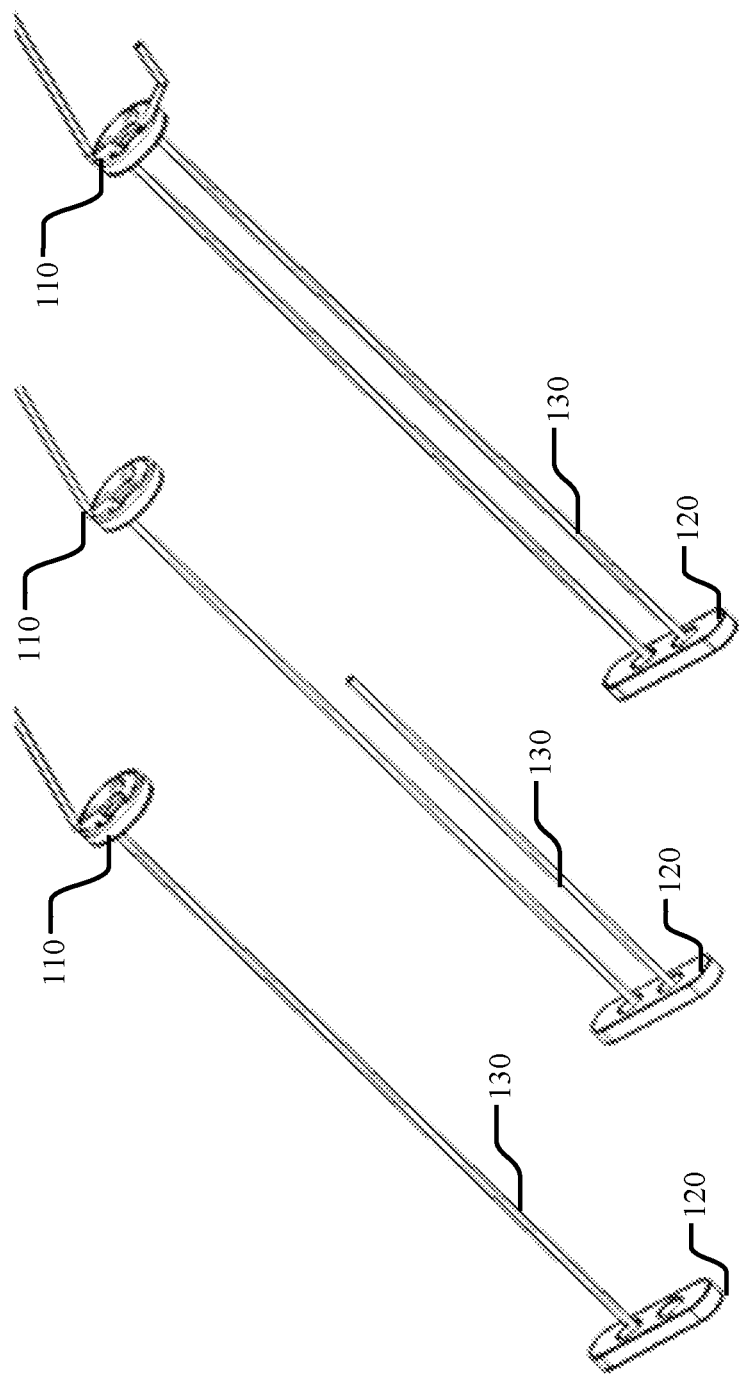

SUTURE BASED CLAMPING DEVICE

CROSS-REFERENCE

This application is a continuation of U.S. application Ser. No. 17/651,747, filed Feb. 18, 2022, now issued as U.S. Pat. No. 11,510,665 on Nov. 29, 2022, which is a continuation of International Application No. PCT/US2021/023101, filed Mar. 19, 2021, which claims the benefit of U.S. Provisional Application No. 63/002,272, filed Mar. 30, 2020, each of which are hereby incorporated by reference in their entirety herein.

BACKGROUND

Several medical procedures require the fastening of one bone to another bone. Some such procedures include fixation of acromioclavicular separations due to coracoclavicular ligament disruptions, fixation of dorsal distal radioulnar ligament disruptions, stabilization of the first and second metatarsals for hallux valgus reconstruction, and stabilization of the first and second metacarpal when the trapezium has been excised due to osteoarthritis.

SUMMARY

One aspect provided herein is a suture-button system comprising: a suture strand; a primary button having a plurality of primary apertures and a primary threaded portion, wherein the suture strand is inserted through a first and second primary aperture of the plurality of primary apertures; a secondary button having a plurality of secondary apertures, wherein the suture strand is inserted through a first and second secondary aperture of the plurality of secondary apertures, such that at least one targeted tissue of a subject is clamped between a distal surface of the primary button and a proximal surface of the secondary button upon applying a tension to the suture strand; and a lock having a secondary threaded portion, wherein the secondary threaded portion is removably coupled to the primary threaded portion, wherein coupling the secondary threaded portion of the lock to the threaded portion prevents the suture strand from translating through the plurality of primary apertures, thereby securing the clamping of the targeted tissue.

In some embodiments, the plurality of primary apertures comprises 2, 3, 4, or 5 primary apertures. In some embodiments, the plurality of primary apertures are equally spaced on the primary button. In some embodiments, the plurality of primary apertures are equally spaced on the primary button in a circular array. In some embodiments, the plurality of primary apertures are equally spaced on the primary button in a circular array about the primary threaded portion. In some embodiments, the plurality of primary apertures are equally spaced on the primary button in a circular array about a center axis of the secondary button. In some embodiments, a proximal surface of the primary button comprises a countersink. In some embodiments, the primary threaded portion comprises a female threaded portion. In some embodiments, the secondary threaded portion comprises a male threaded portion. In some embodiments, the primary threaded portion comprises a male threaded portion. In some embodiments, the secondary threaded portion comprises a female threaded portion. In some embodiments, the plurality of secondary apertures comprises 2, 3, 4, or 5 secondary apertures. In some embodiments, a distal surface of the secondary button comprises a channel connecting two or more of the plurality of secondary apertures. In some embodiments, one or more edges of the secondary button are rounded or chamfered. In some embodiments, an aspect ratio between the length and width of the secondary button is about 1:1 to about 4:1. In some embodiments, the lock comprises a head and wherein the secondary threaded portion extends from the head. In some embodiments, a distal surface of the head is tapered outwards from a center axis of the lock. In some embodiments, the distal surface of the head is tapered outwards from a center axis of the lock by about 20° to about 89°. In some embodiments, the suture strand is a #1 size suture, a #2 size suture, a #3 size suture, a #4 size suture, a #5 size suture, a #6 size suture, or a #7 size suture. In some embodiments, the suture strand has a length of about 100 mm to about 1,200 mm. In some embodiments, the system comprises 2, 3, 4, 5, 6 or more suture strands. In some embodiments, the system comprises a first suture strand and a second suture strand, wherein at least a portion of the first suture strand passes within at least a portion of the second suture strand to form a suture bundle. In some embodiments, the portion of the first suture strand that passes within the second suture strand is a mesial portion of the first suture. In some embodiments, the portion of the second suture strand through which the first suture strand passes is a mesial portion of the second suture. In some embodiments, the lock comprises a driver feature, an alignment feature, or both. In some embodiments, the driver feature is opposite the secondary threaded portion. In some embodiments, the driver feature and the alignment feature are generally concentric. In some embodiments, the driver feature is proximal to the alignment feature. In some embodiments, a maximum inner diameter of the driver feature is greater than a maximum inner diameter of the alignment feature. In some embodiments, the driver feature comprises a Philips driver feature, a flathead driver feature, a torx driver feature, a hex driver feature, or a square socket feature. In some embodiments, the alignment feature has a cross sectional shape comprising a circle, a triangle, a square, a pentagon, a hexagon, an octagon, or any combination thereof. In some embodiments, the system further comprises a lock driver comprising a driving feature that is configured to rotate the lock relative to the primary button. In some embodiments, the lock driver further comprises an aligning feature configured to align the lock driver to the alignment feature of the lock. In some embodiments, the alignment feature is distal to the driving feature. In some embodiments, at least a portion of the lock extends beyond a distal face of the primary button when the primary button is coupled to the lock. In some embodiments, a distal face of the primary button extends beyond a distal face of the lock when the primary button is coupled to the lock. In some embodiments, wherein at least one end of the suture strand is coupled to a terminator. In some embodiments: the system comprises two suture strands, wherein the plurality of primary apertures comprises four primary apertures; the plurality of secondary apertures comprises two secondary apertures; a first suture strand is inserted through a first primary aperture, through a first secondary aperture, through a second secondary aperture, and through a second primary aperture; and a second suture strand is inserted through a third primary aperture, through the first secondary aperture, through the second secondary aperture, and through a fourth primary aperture. In some embodiments: the system comprises two suture strands, wherein the plurality of primary apertures comprises four primary apertures; the plurality of secondary apertures comprises two secondary apertures; a first suture strand is inserted through a first primary aperture, through a first secondary aperture, through a second secondary aperture, and through a second primary aperture; and a second suture strand is inserted through a third primary aperture, through the second secondary aperture, through the first secondary aperture, and through a fourth primary aperture; In some embodiments, the first primary aperture and the second primary aperture are adjacent. In some embodiments, the first primary aperture and the second primary aperture are nonadjacent. In some embodiments, the system further comprises a tightening tool comprising: a threaded rod; a knob coupled to a proximal end of the threaded rod; a collar coupled to the threaded rod; an arm spinner between the knob and the collar, wherein the arm spinner comprises an aperture accepting the threaded rod; and a handle comprising a cavity, wherein at least a portion of the cavity comprises a threaded feature configured to couple to the threaded rod, wherein the lock comprises the driver feature, and wherein a distal portion of the handle comprises a tensioning feature configured to rotate the driving feature of the lock. In some embodiments, the arm spinner further comprises a terminator channel accepting the terminator. In some embodiments, the arm spinner comprises 1, 2, 3, 4, 5, 6, or more terminator channels. In some embodiments, the knob is coupled to the proximal end of the threaded rod by a pin, an adhesive, a fastener, a press-fit, a weld, or any combination thereof. In some embodiments, the collar is coupled to the threaded rod by a pin, an adhesive, a fastener, a press-fit, a weld, or any combination thereof. In some embodiments, the lock further comprises the alignment feature, and wherein the distal portion of the handle further comprises a tensioning alignment feature that couples to the alignment feature. In some embodiments, the arm spinner rotates freely about the threaded rod, the knob, or both. In some embodiments, rotating the knob and the threaded rod in a first direction with respect with to the handle translates the spinner proximally from the handle. In some embodiments, rotating the knob and the threaded rod in a second direction opposite the first direction translates the spinner distally to the handle. In some embodiments, rotating the handle in a first direction tightens the lock against the primary button.

Another aspect provided herein is a suture-button system comprising: one or more a suture strands; a primary button having a plurality of primary apertures, and a primary threaded portion; a secondary button having a plurality of secondary apertures; and a lock having a secondary threaded portion, wherein the secondary threaded portion is removably coupled to the primary threaded portion; wherein each primary aperture has one or more of the plurality of sutures strands inserted therethrough, wherein each secondary aperture has one or more of the plurality of sutures strands inserted therethrough, and wherein coupling the secondary threaded portion of the lock to the threaded portion prevents each of the plurality of suture strands from translating through one or more of the plurality of first button apertures. In some embodiments, the plurality of primary apertures comprises 2, 3, 4, or 5 primary apertures. In some embodiments, the plurality of primary apertures are equally spaced on the primary button. In some embodiments, the plurality of primary apertures are equally spaced on the primary button in a circular array. In some embodiments, the plurality of primary apertures are equally spaced on the primary button in a circular array about the primary threaded portion. In some embodiments, the plurality of primary apertures are equally spaced on the primary button in a circular array about a center axis of the secondary button. In some embodiments, a proximal surface of the primary button comprises a countersink. In some embodiments, the primary threaded portion comprises a female threaded portion. In some embodiments, the secondary threaded portion comprises a male threaded portion. In some embodiments, the primary threaded portion comprises a male threaded portion. In some embodiments, the secondary threaded portion comprises a female threaded portion. In some embodiments, the plurality of secondary apertures comprises 2, 3, 4, or 5 secondary apertures. In some embodiments, a distal surface of the secondary button comprises a channel connecting two or more of the plurality of secondary apertures. In some embodiments, one or more edges of the secondary button are rounded or chamfered. In some embodiments, an aspect ratio between the length and width of the secondary button is about 1:1 so about 4:1. In some embodiments, the lock comprises a head and wherein the secondary threaded portion extends from the head. In some embodiments, a distal surface of the head is tapered outwards from a center axis of the lock. In some embodiments, the distal surface of the head is tapered outwards from a center of the lock by about 20° to about 89°. In some embodiments, the lock comprises a driver feature, an alignment feature, or both. In some embodiments, the driver feature is opposite the secondary threaded portion. In some embodiments, the driver feature and the alignment feature are generally concentric. In some embodiments, the driver feature is proximal to the alignment feature. In some embodiments, a maximum inner diameter of the driver feature is greater than a maximum inner diameter of the alignment feature. In some embodiments, the driver feature comprises a Philips driver feature, a flathead driver feature, a torx driver feature, a hex driver feature, or a square socket feature. In some embodiments, the alignment feature has a cross sectional shape comprising a circle, a triangle, a square, a pentagon, a hexagon, an octagon, or any combination thereof. In some embodiments, they system further comprises a lock driver comprising a driving feature that is configured to rotate the lock about the primary button. In some embodiments, the lock driver further comprises an aligning feature configured to align the lock driver to the alignment feature of the lock. In some embodiments, the alignment feature is distal to the driving feature. In some embodiments, at least a portion of the lock extends beyond a distal face of the primary button when the primary button is coupled to the lock. In some embodiments, a distal face of the primary button extends beyond a distal face of the lock when the primary button is coupled to the lock. In some embodiments: the plurality of primary apertures comprises two primary apertures; the plurality of secondary apertures comprises two secondary apertures; the one or more suture strands consists of one suture strand; and the one suture strand is inserted through a first primary aperture, through a first secondary aperture, through a second secondary aperture, and through a second primary aperture. In some embodiments: the plurality of primary apertures comprises four primary apertures; the plurality of secondary apertures comprises two secondary apertures; the one or more a suture strands consists of two suture strands; a first suture strand is inserted through a first primary aperture, through a first secondary aperture, through a second secondary aperture, and through a second primary aperture; and a second suture strand is inserted through a third primary aperture, through the first secondary aperture, through the second secondary aperture, and through a fourth primary aperture; In some embodiments: the plurality of primary apertures comprises four primary apertures; the plurality of secondary apertures comprises two secondary apertures; the one or more a suture strands consists of two suture strands; a first suture strand is inserted through a first primary aperture, through a first secondary aperture, through a second secondary aperture, and through a second primary aperture; and a second suture strand is inserted through a third primary aperture, through the second secondary aperture, through the first secondary aperture, and through a fourth primary aperture; In some embodiments, the first primary aperture and the second primary aperture are adjacent. In some embodiments, the first primary aperture and the second primary aperture are nonadjacent. In some embodiments, the system further comprises a tightening tool comprising: a threaded rod; a knob coupled to a proximal end of the threaded rod; a collar coupled to the threaded rod; an arm spinner between the knob and the tensioning collar, wherein the arm spinner comprises an aperture accepting the threaded rod; and a handle comprising a cavity, wherein at least a portion of the cavity comprises a threaded feature configured to couple to the threaded rod, wherein the lock comprises the driver feature, and wherein a distal portion of the handle comprises a tensioning feature configured to rotate the driving feature of the lock. In some embodiments, the arm spinner further comprises a terminator channel accepting the terminator. In some embodiments, the arm spinner comprises 1, 2, 3, 4, 5, 6, or more terminator channels. In some embodiments, the knob is coupled to the proximal end of the threaded rod by a pin, an adhesive, a fastener, a press-fit, a weld, or any combination thereof. In some embodiments, the collar is coupled to the threaded rod by a pin, an adhesive, a fastener, a press-fit, a weld, or any combination thereof. In some embodiments, the lock further comprises the alignment feature, and wherein the distal portion of the handle further comprises a tensioning alignment feature that couples to the alignment feature. In some embodiments, the arm spinner rotates freely about the threaded rod, the knob, or both. In some embodiments, rotating the knob and the threaded rod in a first direction with respect with to the handle translates the spinner proximally from the handle. In some embodiments, rotating the knob and the threaded rod in a second direction opposite the first direction translates the spinner distally towards the handle. In some embodiments, rotating the handle in a first direction tightens the lock against the primary button. In some embodiments, the suture is a #1 size suture, a #2 size suture, a #3 size suture, a #4 size suture, a #5 size suture, a #6 size suture, or a #7 size suture. In some embodiments, the suture has a length of about 100 mm to about 1,200 mm. In some embodiments, the system comprise 2, 3, 4, 5, 6 or more suture strands. In some embodiments, the system comprise a first suture strand and a second suture strand, wherein at least a portion of the first suture strand passes within at least a portion of the second suture strand to form a suture bundle 170. In some embodiments, the portion of the first suture strand that passes within the second suture strand is a mesial portion of the first suture. In some embodiments, the portion of the second suture strand through which the first suture strand passes is a mesial portion of the second suture.

Another aspect provided herein is a suture-button assembly comprising: two or more suture-button systems; and an insertion plate comprising a plurality of insertion plate apertures, each insertion plate aperture accepting at least one suture strand. In some embodiments, the plurality of insertion plate apertures comprises 2, 3, 4, 5, 6, or more insertion plate apertures. In some embodiments, the assembly further comprises an insertion screw, wherein the insertion plate further comprises a screw hole; configured to removable couple to the insertion screw. In some embodiments, the screw hole is positioned between two of the plurality of insertion plate apertures. In some embodiments, the insertion screw comprises a first portion configured to removably couple to the screw hole and a second portion configured to attach to a bone of a patient.

Another aspect provided herein is a method of assembling a suture button, the method comprising: providing the suture-button system of any one or more embodiments described herein, wherein: the plurality of primary apertures comprises a first primary aperture and a second primary aperture; the plurality of secondary apertures comprises a first secondary aperture and a second secondary aperture; and the one or more a suture strands consists of one suture strand; inserting the one suture strand through the first primary aperture; inserting the one suture strand through the first secondary aperture; inserting the one suture strand through the second secondary aperture; and inserting the one suture strand through the second primary aperture. In some embodiments, the method further comprises inserting the secondary button through a hole in a bone or tissue. In some embodiments, the method further comprises rotating the secondary button after its insertion through the hole in the bone or tissue such that a proximal face of the secondary button lies against the bone or tissue. In some embodiments, the method further comprises coupling the secondary threaded portion of the lock with the primary threaded portion of the primary button to prevent the suture strand from translating through the first primary aperture and the second primary aperture. In some embodiments, the method further comprises providing the tightening tool of any one or more embodiments described herein. In some embodiments, the secondary threaded portion and the primary threaded portion are coupled by the tightening tool. In some embodiments, the method further comprises tightening the suture strand with respect to the primary button, the secondary button, or both, with the tightening tool.

Another aspect provided herein is a method of assembling a suture button, the method comprising: providing the suture-button system of any one or more embodiments described herein, wherein: the plurality of primary apertures comprises a first primary aperture, a second primary aperture, a third primary aperture, and a fourth primary aperture; the plurality of secondary apertures comprises a first secondary aperture and a second secondary aperture; and the one or more suture strands consists of a first suture strand and a second suture strand; inserting the first suture strand through the first primary aperture; inserting the first suture strand through the first secondary aperture; inserting the first suture strand through the second secondary aperture; inserting the first suture strand through the second primary aperture; inserting the second suture strand through the third primary aperture; inserting the second suture strand through the first secondary aperture; inserting the second suture strand through the second secondary aperture; and inserting the second suture strand through the fourth primary aperture. In some embodiments, the method further comprises inserting the secondary button through a hole in a bone or tissue. In some embodiments, the method further comprises rotating the secondary button after its insertion through the hole in the bone or tissue such that a proximal face of the secondary button lies against the bone or tissue. In some embodiments, the method further comprises coupling the secondary threaded portion of the lock with the primary threaded portion of the primary button to prevent the first suture strand and the second suture strand from translating through the plurality of primary apertures. In some embodiments, the method further comprises providing the tightening tool of any one or more embodiments described herein. In some embodiments, the secondary threaded portion and the primary threaded portion are coupled by the tightening tool. In some embodiments, the method further comprises tightening the first suture strand and the second suture strand with respect to the primary button, the secondary button, or both, with the tightening tool.

Another aspect provided herein is a method of assembling a suture button, the method comprising: providing the suture-button system of any one or more embodiments described herein, wherein: the plurality of primary apertures comprises a first primary aperture, a second primary aperture, a third primary aperture, and a fourth primary aperture; the plurality of secondary apertures comprises a first secondary aperture and a second secondary aperture; and the one or more a suture strands consists of a first suture strand and a second suture strand; inserting the first suture strand through the first primary aperture; inserting the first suture strand through the first secondary aperture; inserting the first suture strand through the second secondary aperture; inserting the first suture strand through the second primary aperture; inserting the second suture strand through the third primary aperture; inserting the second suture strand through the second secondary aperture; inserting the second suture strand through the first secondary aperture; and inserting the second suture strand through the fourth primary aperture. In some embodiments, the method further comprises inserting the secondary button through a hole in a bone or tissue. In some embodiments, the method further comprises rotating the secondary button after its insertion through the hole in the bone or tissue such that a proximal face of the secondary button lies against the bone or tissue. In some embodiments, the method further comprises coupling the secondary threaded portion of the lock with the primary threaded portion of the primary button to prevent the first suture strand and the second suture strand from translating through the plurality of primary apertures. In some embodiments, the method further comprises providing the tightening tool of any one or more embodiments described herein. In some embodiments, the secondary threaded portion and the primary threaded portion are coupled by the tightening tool. In some embodiments, the method further comprises tightening the first suture strand and the second suture strand with respect to the primary button, the secondary button, or both, with the tightening tool.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 25A shows a perspective illustration of the exemplary insertion plate, per an embodiment herein;

FIG. 25B shows a detailed top-right-front illustration of the exemplary insertion plate, per an embodiment herein;

FIG. 25C shows a cross-section illustration of the exemplary insertion plate, per an embodiment herein;

FIG. 26A shows a perspective illustration of an insertion screw, per an embodiment herein;

FIG. 26B shows a front-view illustration of an insertion screw, per an embodiment herein;

FIG. 27A shows a perspective illustration of inserting a suture strand through a first primary aperture of the primary button, per an embodiment herein;

FIG. 27B shows a perspective illustration of inserting a suture strand through a first and second secondary aperture of the secondary button, per an embodiment herein;

FIG. 27C shows a perspective illustration of inserting a suture strand through a second primary aperture of the primary button, per an embodiment herein;

DETAILED DESCRIPTION

Figure 1:
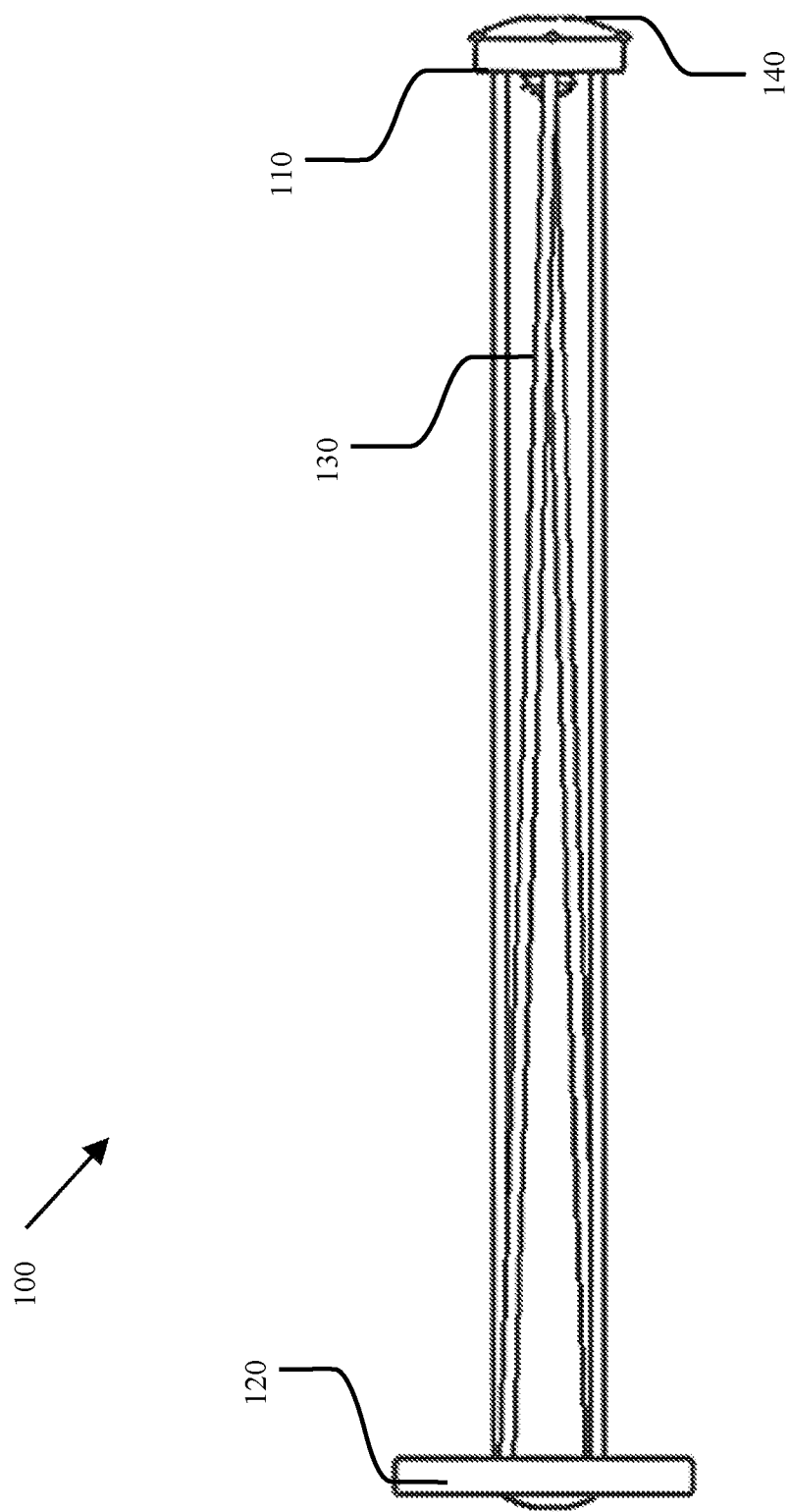
FIG. 1 shows a front-view illustration of an exemplary suture-button assembly, per an embodiment herein.

Potential applications of the devices, systems, and methods herein include but are not limited to fixation of acromioclavicular separations due to coracoclavicular ligament disruptions, fixation of dorsal distal radioulnar ligament disruptions, stabilization of the first and second metatarsals for hallux valgus reconstruction, and stabilization of the first and second metacarpal when the trapezium has been excised due to osteoarthritis.

Suture-Button Systems

One aspect provided herein per FIGS. 1-13B is a suture-button system 100. In some embodiments, the suture-button system comprises one or more suture strands 130, a primary button 110, a secondary button 120, and a lock 140. In some embodiments, the lock 140 couples to the primary button 110.

In some embodiments, the suture strand 130 is a standard suture. In some embodiments, the suture strand 130 is a medical grade suture. In some embodiments, the suture is a #1 size suture, a #2 size suture, a #3 size suture, a #4 size suture, a #5 size suture, a #6 size suture, or a #7 size suture. In some embodiments, the suture strand 130 has a length of about 100 mm to about 1,200 mm. In some embodiments, the system 100 comprises 2, 3, 4, 5, 6 or more suture strands 130. As disclosed herein, the terms suture and suture strands are used interchangeably.

In some embodiments, per FIGS. 1-4, and 10A-13, the system 100 comprises a first suture strand 130 and a second suture strand 130. In some embodiments, the first suture strand 130 and the second suture strand 130 are bundled 170 together. In some embodiments, per FIGS. 10A and 10B, at least a portion of the second suture strand 130 is hollow or comprises a channel, wherein at least a portion of the first suture strand 130 passes within at least a portion of the hollow portion or the channel of the second suture strand 130 to form a suture bundle 170. In some embodiments, the portion of the first suture strand 130 that passes within the second suture strand 130 is a mesial portion of the first suture. In some embodiments, the portion of the second suture strand 130 through which the first suture strand 130 passes is a mesial portion of the second suture. Alternatively, in some embodiments, the system 100 comprises three or more suture strands 130, wherein one or more of the three or more suture strands 130 are bundled 170 together. In some embodiments, bundling the suture strands 130 together reduces fraying upon contact and/or movement with respect to the secondary button 120. In some embodiments, one or two of the three or more suture strands 130 pass within one or two other passes within at least a portion of another suture strand 130.

In some embodiments, per FIGS. 11A-13, two ends of a suture strand 130 are coupled to each other. Further, in some embodiments two ends of a suture strand 130 are coupled to each other to form a suture loop 132. In some embodiments, two ends of a suture strand 130 are tied together in a knot to form a suture loop. In some embodiments, per FIG. 12, two ends of a suture strand 130 are coupled to each other by a terminator 131. In some embodiments, at least one end of a suture strand 130 is coupled to the terminator 131. In some embodiments, both ends of a suture strand is coupled to a terminator 131. In some embodiments, the terminator is coupled to both ends of the suture to form a suture loop 132. In some embodiments, the terminator 131 is coupled to both ends of each of two sutures to form two suture loops 132. In some embodiments, the terminator 131 is coupled to the suture by a crimp, a fastener, an adhesive, a tie, or any combination thereof. In some embodiments, an outer diameter of the terminator 131 is greater than twice an outer diameter of the suture strands 130. In some embodiments, the suture loops 132 ease hand tensioning.

In some embodiments, tension applied to one or more suture loops adjusts the distance between the primary and secondary buttons. In some embodiments, tension applied to one or more suture loops brings the primary and secondary buttons closer together. In some embodiments, tension applied to one or more suture loops provides a clamping pressure or force about a bone or tissue located between the primary and secondary buttons. In some embodiments, tension is applied by tightening the one or more suture loops. In some embodiments, the one or more suture loops are tightened by pulling on the one or more suture loops. In some embodiments, the one or more suture loops are pulled in a proximal direction relative to the primary button.

Figure 5:
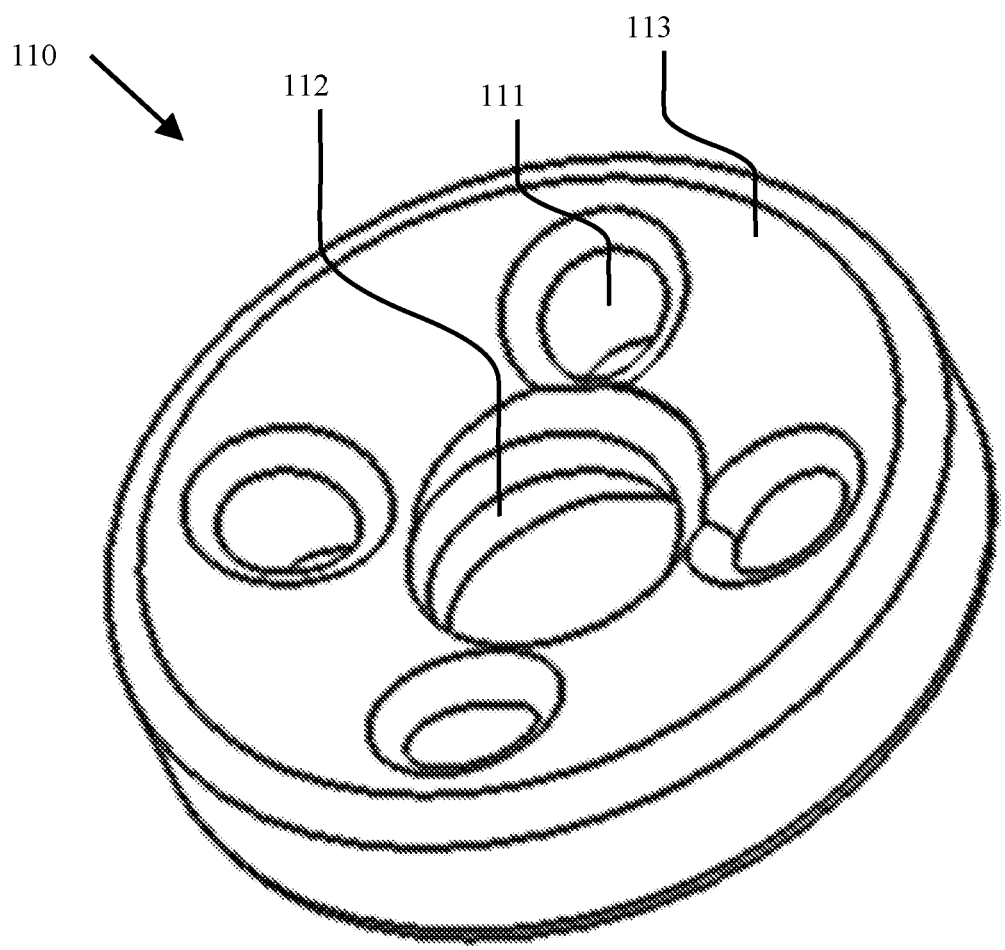
FIG. 5 shows a perspective illustration of an exemplary primary button, per an embodiment herein.

In some embodiments, per FIGS. 5 and 6, the primary button 110 comprises four primary apertures 111 and a primary threaded portion 112. Alternatively, in some embodiments, the primary button 110 comprises 2, 3, 5, 6, or more primary apertures 111. Further, per FIGS. 5 and 6, the four primary apertures 111 are equally spaced apart on the primary button 110 in a circular array about the primary threaded portion 112 and/or about a center axis of the secondary button 120. As shown, the primary apertures 111 are circular. Alternatively, the primary apertures 111 are oblong or polygonal.

Figure 6A:
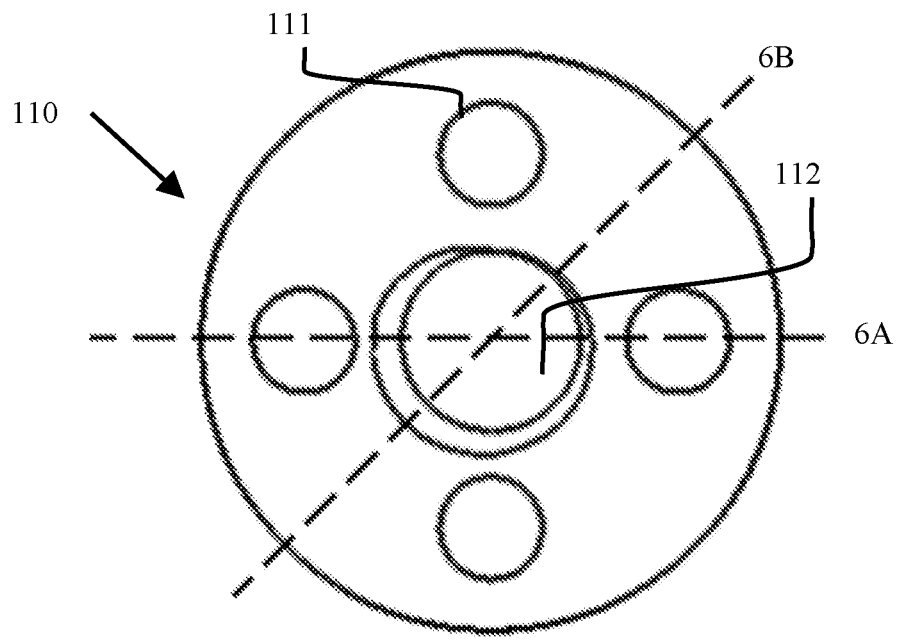
FIG. 6A shows a bottom-view illustration of an exemplary primary button, per an embodiment herein.
Figure 6B:
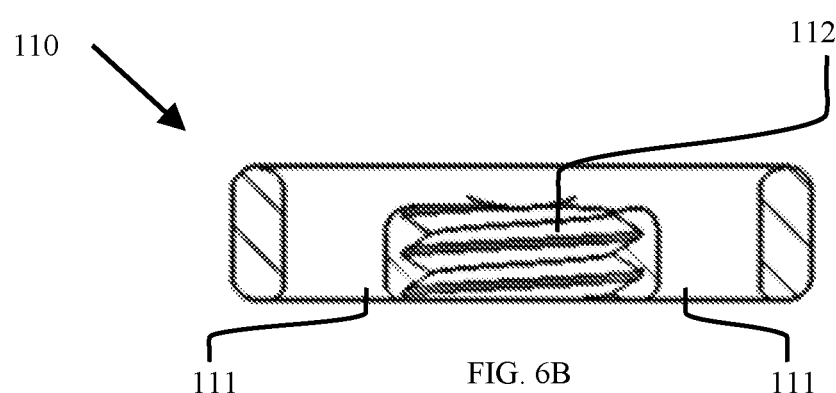
FIG. 6B shows a first cross-sectional illustration of an exemplary primary button, per an embodiment herein.
Figure 6C:
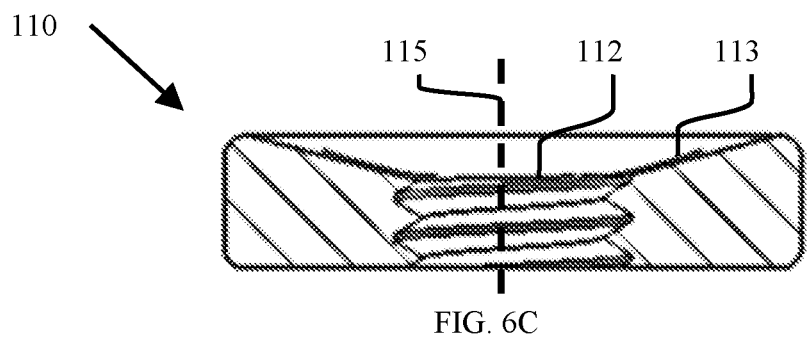
FIG. 6C shows a second cross-sectional illustration of an exemplary primary button, per an embodiment herein.
Figure 8:
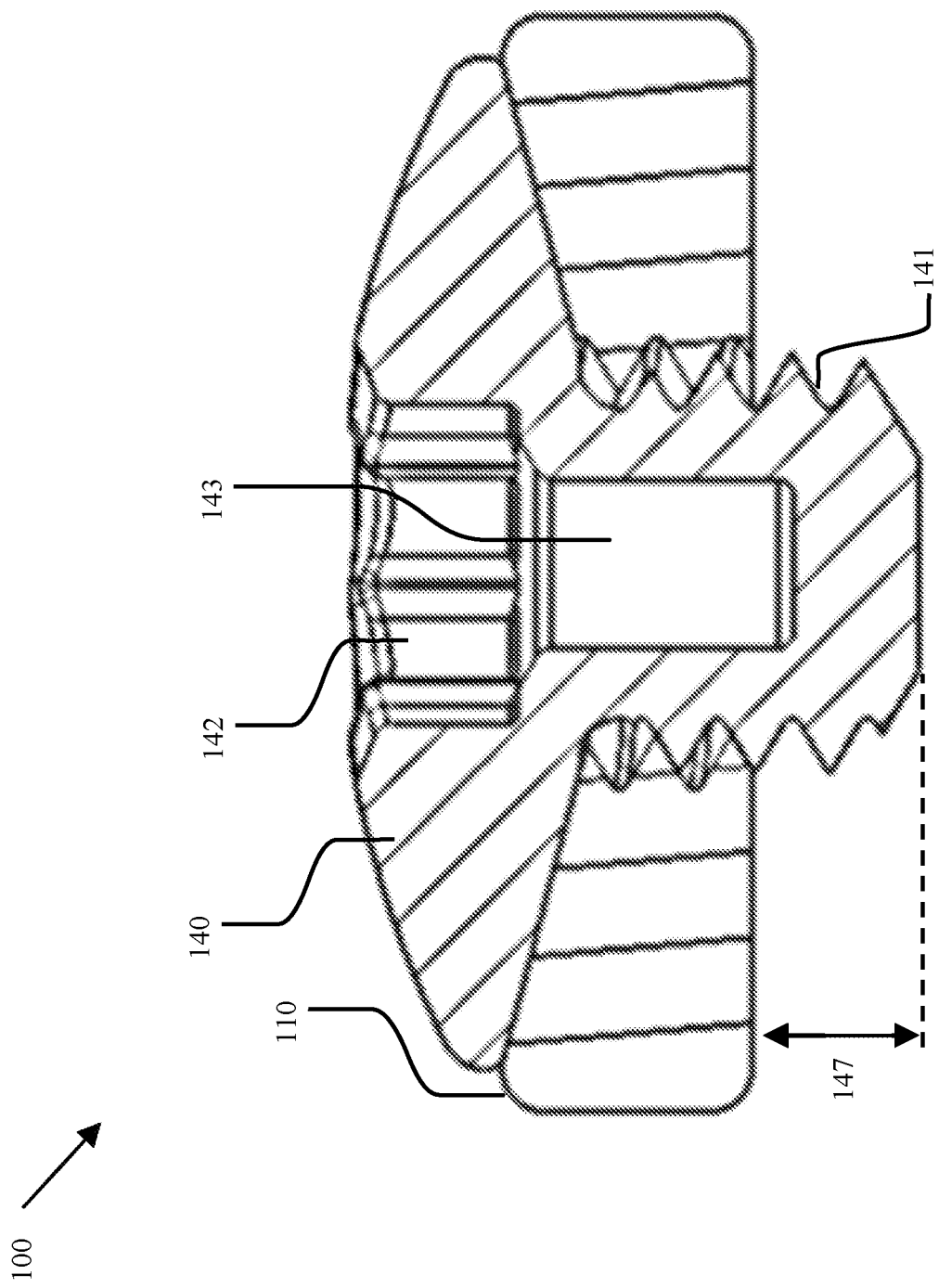
FIG. 8 shows a cross-sectional illustration of an exemplary lock coupled to an exemplary primary button, per an embodiment herein.

In some embodiments, per FIGS. 5, 6C, and 8, a proximal surface 113 of the primary button 110 is tapered towards the primary threaded portion 112. In some embodiments, per FIG. 6C, the proximal surface 113 of the primary button 110 is tapered at an angle of about 30°, about 35°, about 40°, about 45°, about 50°, about 55°, about 60°, about 65°, about 70°, about 75°, about 80°, or about 85° relative to a central axis 115 concentric to the primary threaded portion 112. In some embodiments, the proximal surface 113 of the primary button 110 is tapered at an angle of about 30 to about 85°, including increments therein, relative to a central axis 115 concentric to the primary threaded portion. In some embodiments, the primary button proximal surface 113 is tapered at an angle of about 20° to about 89° relative to the central axis through the primary threaded portion.

As shown in FIGS. 5, 6A-C, and 8, the primary threaded portion 112 comprises a female threaded portion. Further as shown, the primary threaded portion 112 is centered within the proximal surface 113 of the primary button 110. Alternatively, in some embodiments, the primary threaded portion 112 comprises a male threaded portion. In some embodiments, the primary threaded portion 112 comprises a straight threaded portion. In some embodiments, the primary threaded portion 112 comprises a tapered threaded portion. In some embodiments, the primary threaded portion 112 comprises a machine threaded portion. In some embodiments, the primary threaded portion 112 comprises a pipe threaded portion.

In some embodiments, one or more outer edges of the primary button 110 are rounded or chamfered. In some embodiments, one or more edges of the apertures 111 on a distal face of the primary button 110 are rounded or chamfered. In some embodiments, one or more edges of the primary apertures 111 on a proximal face of the primary button 110 are rounded or chamfered. In some embodiments, one or more edges of the primary button 110 are rounded or chamfered. In some embodiments, the rounded or chamfered edges reduce and/or prevent damage to a portion of suture strand 130 passing thereover.

Figure 9A:
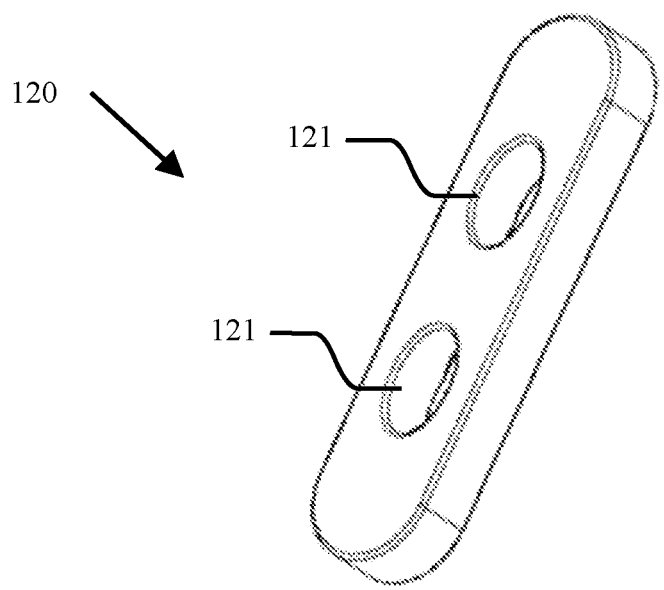
FIG. 9A shows a perspective illustration of an exemplary secondary button, per an embodiment herein.
Figure 9B:
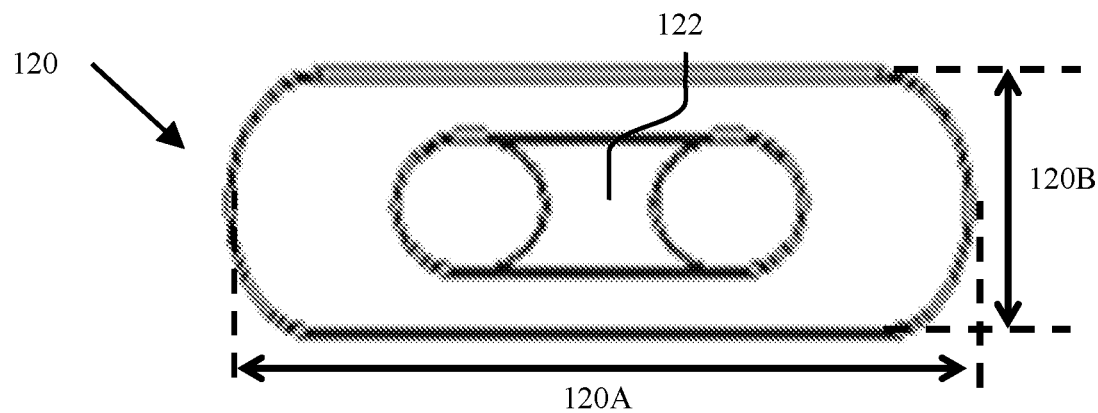
FIG. 9B shows a bottom-view illustration of an exemplary secondary button, per an embodiment herein.
Figure 9C:
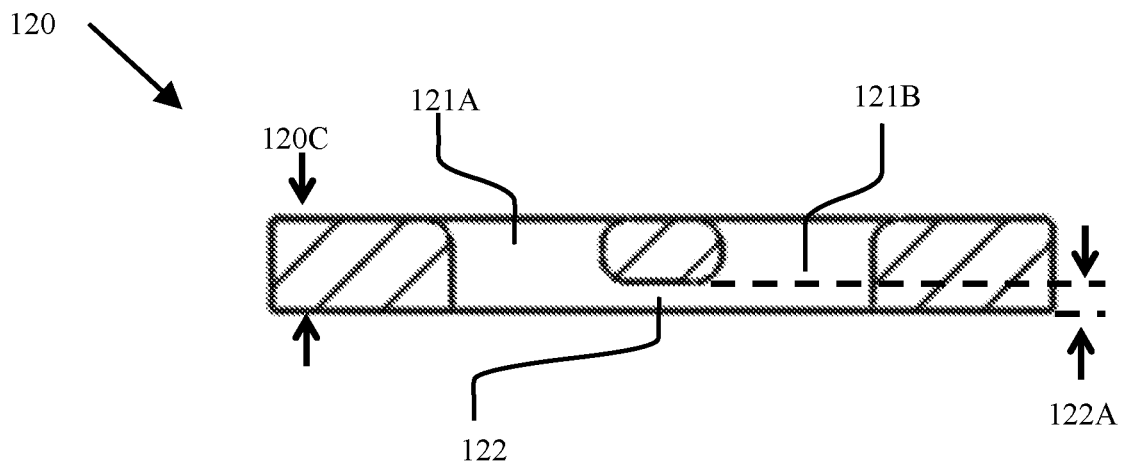
FIG. 9C shows a cross-sectional illustration of an exemplary secondary button, per an embodiment herein.
Figure 10A:
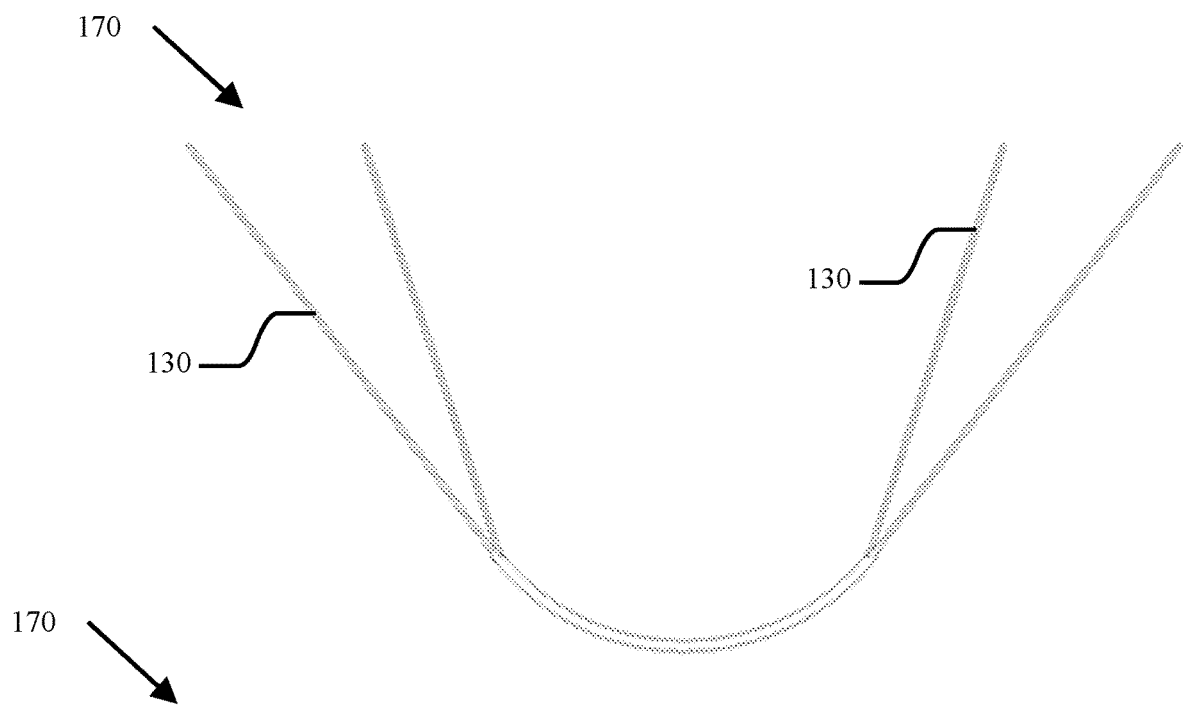
FIG. 10A shows a perspective illustration of an exemplary bundle 170 of sutures, per an embodiment herein.
Figure 10B:
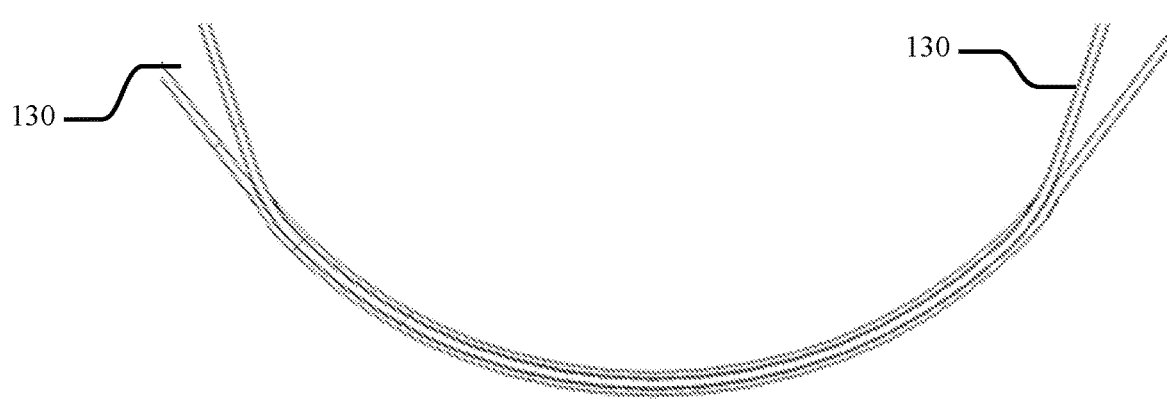
FIG. 10B shows a cross-sectioned illustration of an exemplary bundle 170 of sutures, per an embodiment herein.

As shown in FIGS. 9A-C, the secondary button 120 comprises a first secondary aperture 121 and a second secondary aperture 121. Alternatively, in some embodiments, the plurality of secondary apertures 121 comprises 3, 4, 5, 6, or more secondary apertures 121. As shown, the secondary apertures 121 are oblong. Alternatively, the secondary apertures 121 are circular or polygonal. In some embodiments, each secondary aperture 121 accepts one or more suture strands 130 therethrough. In some embodiments, each secondary aperture 121 accepts 1, 2, 3, 4, 5, 6 or more suture strands 130 therethrough. In some embodiments, per FIGS. 9B-C, a distal surface of the secondary button 120 comprises a channel 122 connecting two or more of the plurality of secondary apertures 121. As seen the channel 122 has a width equal to an inner width of the first secondary aperture 121, the second secondary aperture 121, or both. In some embodiments, the channel 122 has a depth 122A of about 25% to about 75% of the thickness 120C of the secondary button 120. In some embodiments, an aspect ratio between the length 120A and width 120B of the secondary button 120 is about 1:1 to about 4:1. In some embodiments, the aspect ratio and/or thickness 120C of the secondary button 120 enables its insertion through a narrow cavity in a bone.

In some embodiments, the primary button 110 has a width of about 3 mm to about 12 mm. In some embodiments, the primary button 110 has a length of about 3 mm to about 12 mm. In some embodiments, the primary button 110 has a diameter of about 3 mm to about 12 mm. In some embodiments, the primary button 110 has a thickness of about 0.5 mm to about 3 mm. In some embodiments, the secondary button 120 has a width of about 2 mm to about 7 mm. In some embodiments, the secondary button 120 has a length of about 7 mm to about 20 mm. In some embodiments, the secondary button 120 has a thickness of about 0.5 mm to about 3 mm.

Further per FIG. 9C, in some embodiments, one or more edges of the secondary button 120 are rounded or chamfered. In some embodiments, one or more outer edges of the secondary button 120 are rounded or chamfered. In some embodiments, one or more edges of the secondary apertures 121, the channel 122, or both are rounded or chamfered. In some embodiments, one or more edges of the secondary apertures 121 on a distal face of the secondary button 120 are rounded or chamfered. In some embodiments, one or more edges of the secondary apertures 121 on a proximal face of the secondary button 120 are rounded or chamfered. In some embodiments, the rounded or chamfered edges reduce and/or prevent damage to a portion of suture passing thereover.

In some embodiments, a distance between the centers 121A, 121B of a first secondary aperture 121 and a second secondary aperture 121 is greater than a distance between the centers of at least one pair of opposing primary apertures 111. In some embodiments, a distance between the centers 121A, 121B of the first secondary aperture 121 and the second secondary aperture 121 is less than a distance between the centers of at least one pair of opposing primary apertures 111. In some embodiments, a distance between the centers 121A, 121B of the first secondary aperture 121 and the second secondary aperture 121 is equal to a distance between the centers of at least one pair of opposing primary apertures 111. In some embodiments, a distance between the centers 121A, 121B of the first secondary aperture 121 and the second secondary aperture 121 is greater than a distance between the centers of at least one pair of adjacent primary apertures 111. In some embodiments, a distance between the centers 121A, 121B of the first secondary aperture 121 and the second secondary aperture 121 is less than a distance between the centers of at least one pair of adjacent primary apertures 111. In some embodiments, a distance between the centers 121A, 121B of the first secondary aperture 121 and the second secondary aperture 121 is equal to a distance between the centers of at least one pair of adjacent primary apertures 111.

Per FIGS. 7A-D, the lock 140 comprises a secondary threaded portion 141 and a head 144, wherein the secondary threaded portion 141 extends from the head 144. As shown, the secondary threaded portion 141 comprises a male threaded portion. Alternatively, in some embodiments, the secondary threaded portion 141 comprises a female threaded portion. In some embodiments, the secondary threaded portion 141 comprises a straight threaded portion. In some embodiments, the secondary threaded portion 141 comprises a tapered threaded portion. In some embodiments, the secondary threaded portion 141 comprises a machine threaded portion. In some embodiments, the secondary threaded portion 141 comprises a pipe threaded portion. In some embodiments, the lock 140 comprises a driver feature 142, an alignment feature 143, or both. In some embodiments, the driver feature is disposed at least partially within the head 144. In some embodiments, the driver feature 142 is opposite the secondary threaded portion 141. In some embodiments, the driver feature 142 and the alignment feature 143 are generally concentric. In some embodiments, the driver feature 142 is proximal to the alignment feature 143. In some embodiments, a maximum inner diameter of the driver feature 142 is greater than a maximum inner diameter of the alignment feature 143. In some embodiments, the driver feature comprises a Philips driver feature, a flathead driver feature, a torx driver feature, a hex driver feature, or a square socket feature. In some embodiments, the alignment feature 143 has a cross sectional shape comprising a circle, a triangle, a square, a pentagon, a hexagon, an octagon, or any combination thereof. In some embodiments, a proximal edge of the alignment feature 143 is rounded or chamfered.

Figure 7A:
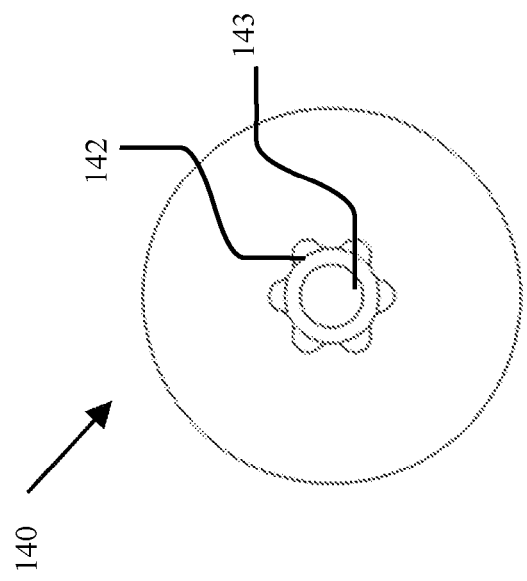
FIG. 7A shows a perspective illustration of an exemplary lock, per an embodiment herein.
Figure 7B:
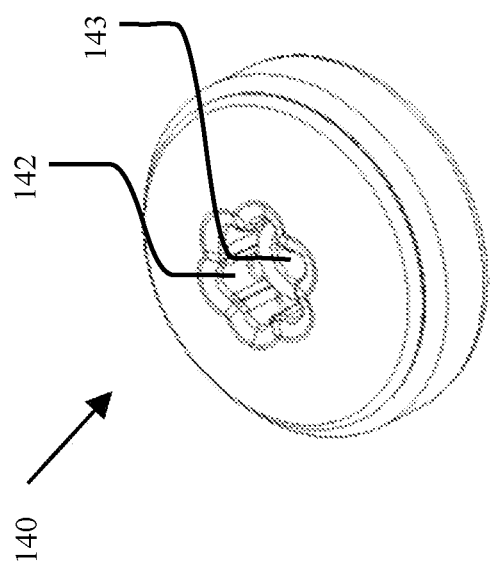
FIG. 7B shows a top-view illustration of an exemplary lock, per an embodiment herein.
Figure 7C:
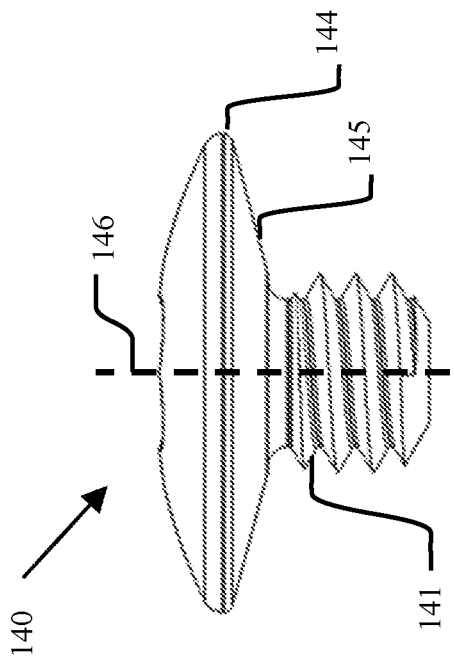
FIG. 7C shows a cross-sectional illustration of an exemplary lock, per an embodiment herein.
Figure 7D:
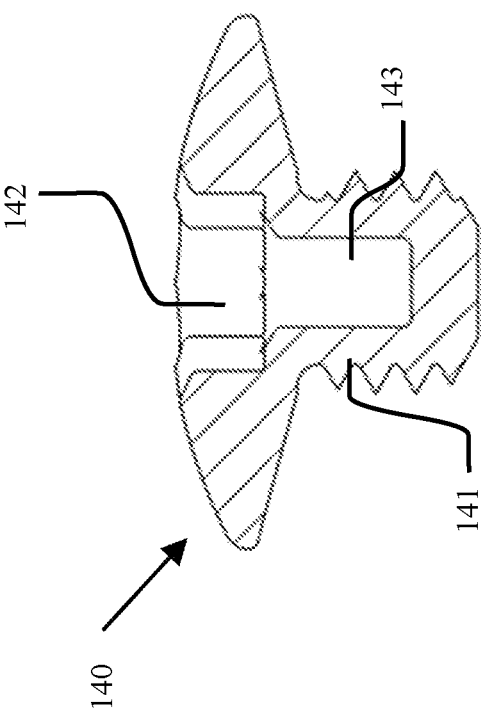
FIG. 7D shows a side view illustration of an exemplary lock, per an embodiment herein.

As shown per FIGS. 7C, 7D, and 8, a distal surface 145 of the head 144 is tapered towards the secondary threaded portion 141. In some embodiments, a distal surface 145 of the head 144 is tapered inward to the center axis 146 of the lock 140. In some embodiments, the distal surface 145 of the head 144 is tapered outwards from the center axis 146 of the lock 140 at an angle of about 20° to about 89° relative to an axis parallel the center axis 146 of the lock 140.

In some embodiments, per FIG. 8, the secondary threaded portion 141 is configured to be removably coupled to the primary threaded portion 112. In some embodiments, coupling the secondary threaded portion 141 of the lock 140 to the primary threaded portion 112 of the primary button 110 prevents the suture strand 130 from translating through one or more of the plurality of first button apertures.

Further per FIG. 8, at least a portion of the tapered distal face 145 of lock 140 seats against the tapered portion of the primary button proximal surface 113 of the primary button 110. In some embodiments, the angle that the distal face of the lock 140 tapers is equivalent to an angle that the primary button proximal face 113 tapers towards the primary threaded portion. In some embodiments, the angle between the proximal surface 113 of the primary button 110 relative to its central axis 115, and the angle between the distal surface 145 of the head 144 relative to the center axis 146 of the lock 140 are complementary. In some embodiments, the angle between the proximal surface 113 of the primary button 110 relative to its central axis 115, and the angle between the distal surface 145 of the head 144 relative to the center axis 146 of the lock 140 are equal. In some embodiments, at least a portion of the distal surface 145 of the head 144, the proximal surface 113 of the primary button 110, or both have a texture configured to increase friction against the suture strand 130.

Figures 11A, 11B:
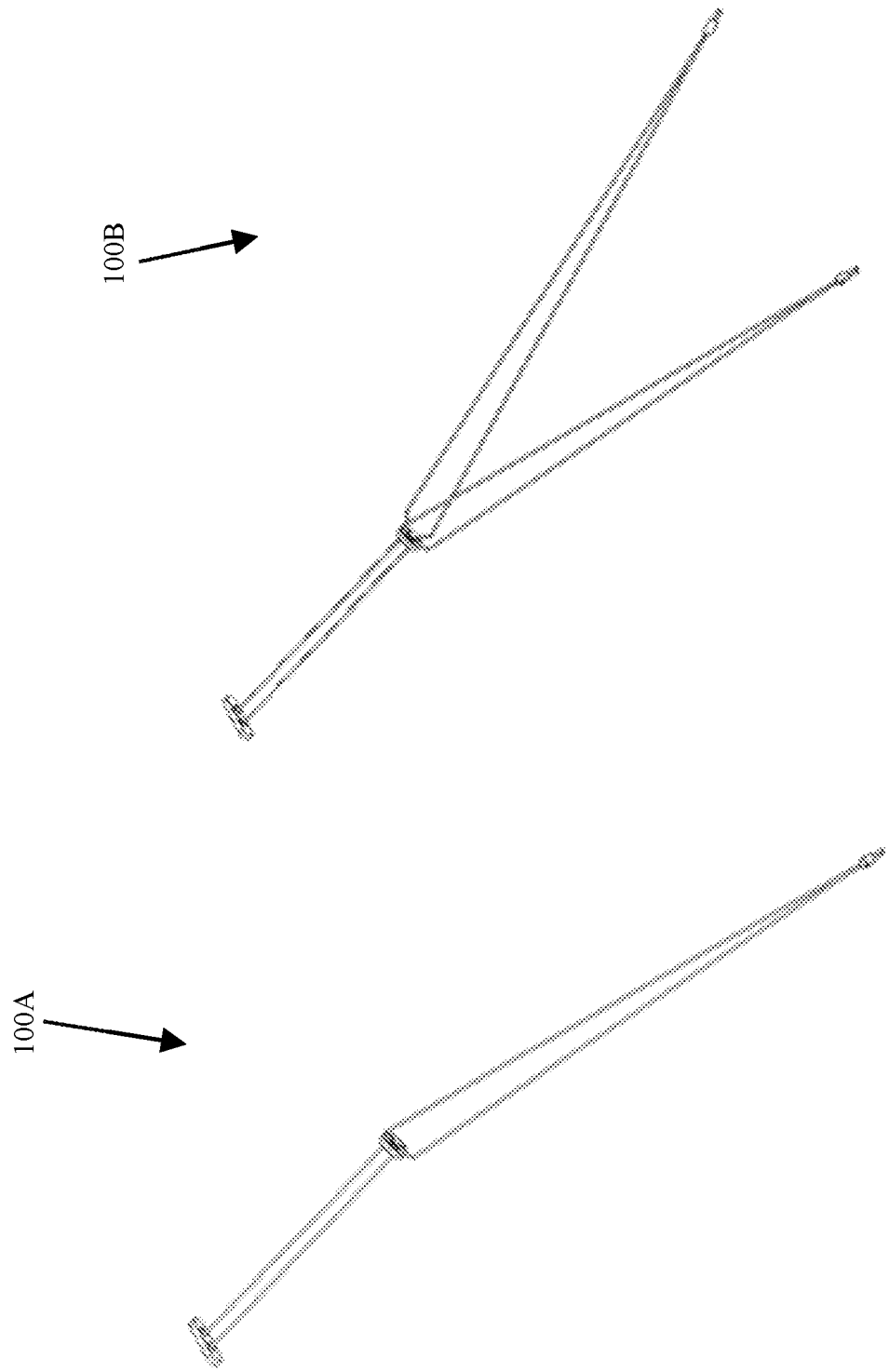
FIG. 11A shows a perspective illustration of an exemplary suture-button assembly with a first suture loop, per an embodiment herein.
FIG. 11B shows a perspective illustration of an exemplary suture-button assembly with a first suture loop and a second suture loop, per an embodiment herein.
Figure 12:
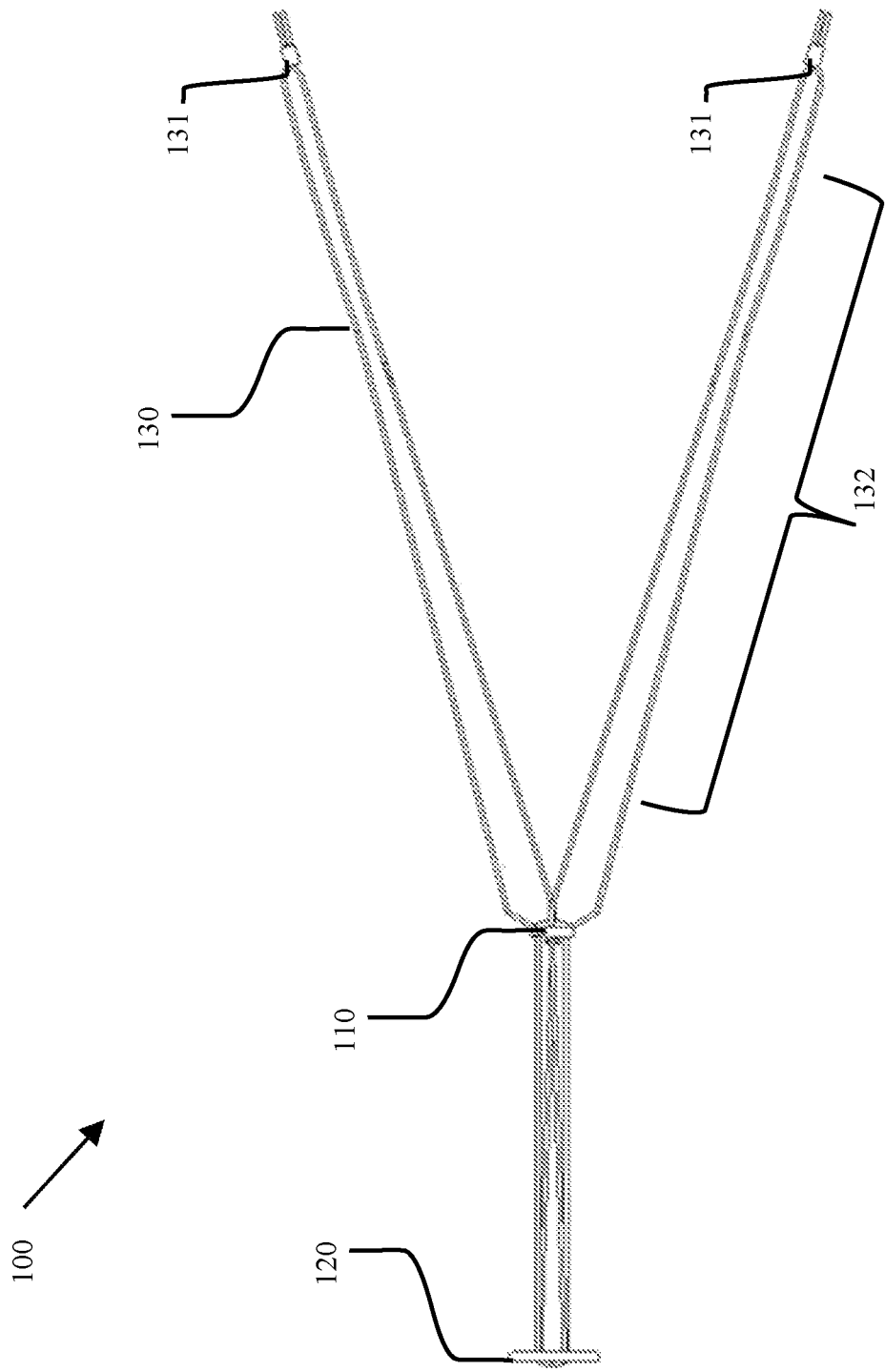
FIG. 12 shows an illustration of an exemplary suture-button assembly with a first suture loop and a second suture loop, per an embodiment herein.

In some embodiments of a first suture-button system 100A, per FIG. 11A, the primary button comprises a first primary aperture and a second primary aperture, the secondary button comprises a first secondary aperture and a second secondary aperture, and a single suture strand passes through the apertures of the primary and secondary buttons. In some embodiments of a second suture-button system 100, per FIGS. 1, 2, 3, 11B and 12, the primary button comprises a first primary aperture, a second primary aperture, a third primary aperture, and a fourth primary aperture, the secondary button comprises a first secondary aperture and a second secondary aperture, and a first suture strand and a second suture strand pass through one or more apertures of the primary and secondary buttons.

Figure 2:
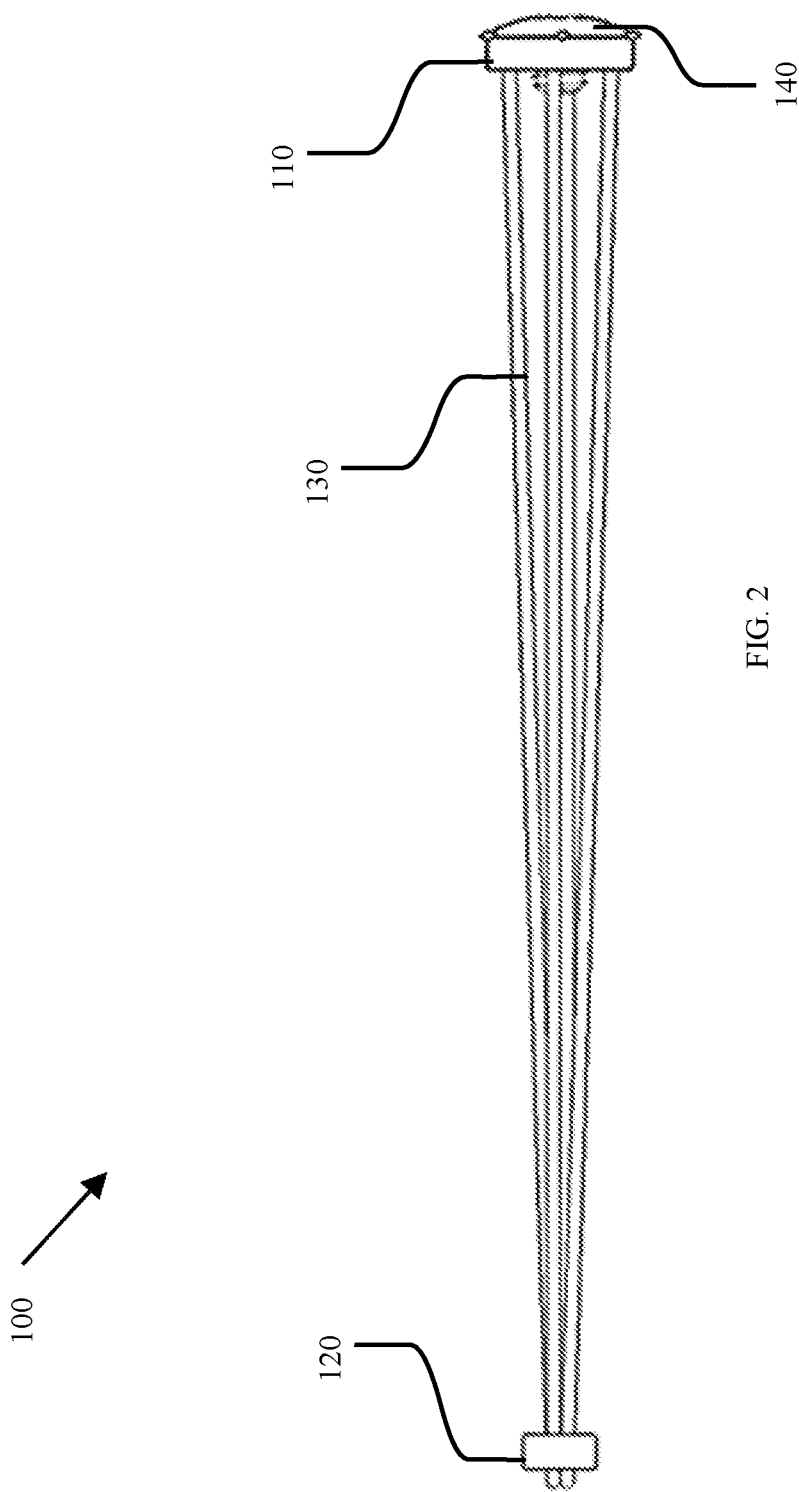
FIG. 2 shows a right-side-view illustration of an exemplary suture-button assembly, per an embodiment herein.
Figure 3:
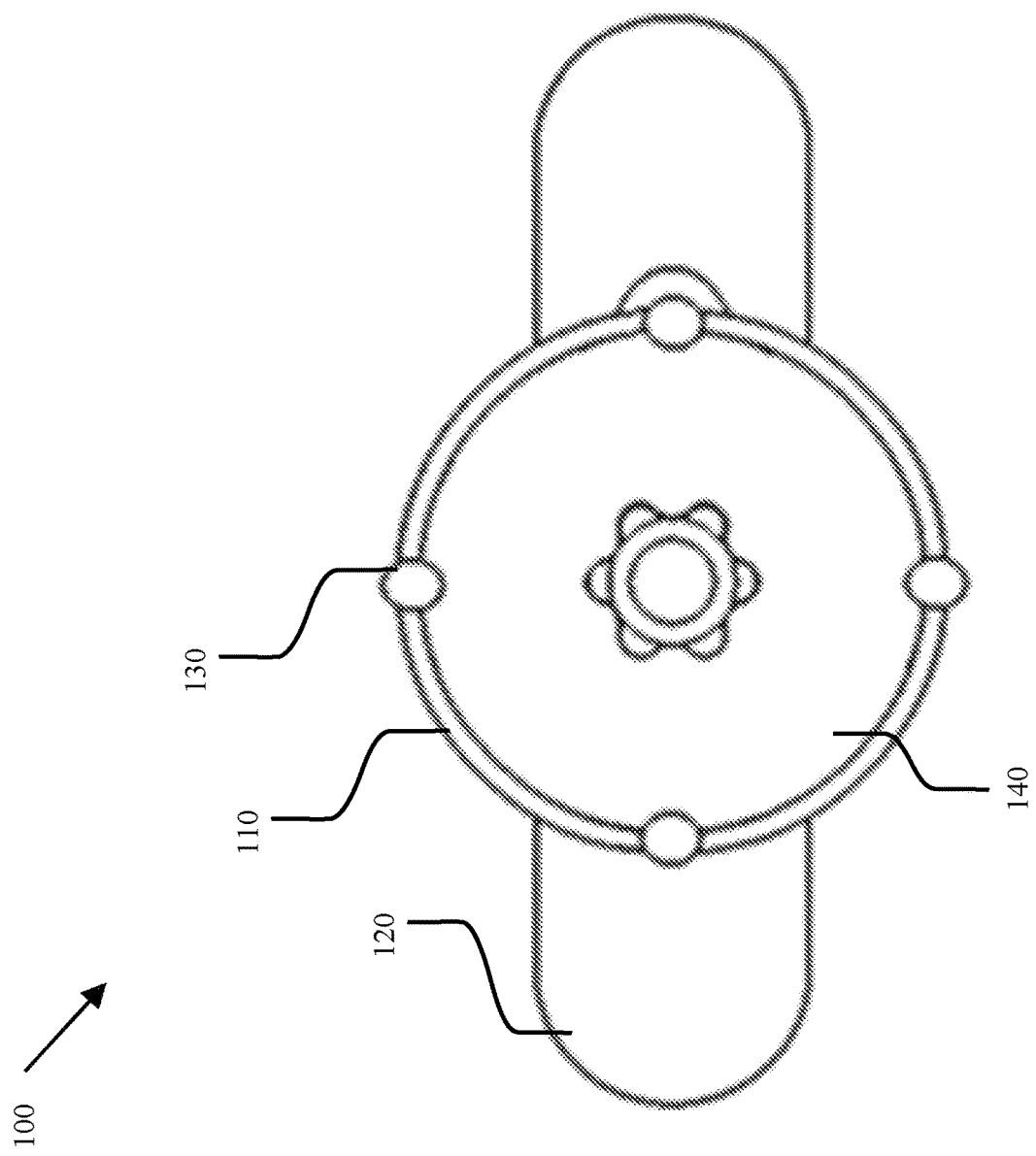
FIG. 3 shows a top-view illustration of an exemplary suture-button assembly, per an embodiment herein.
Figure 4:
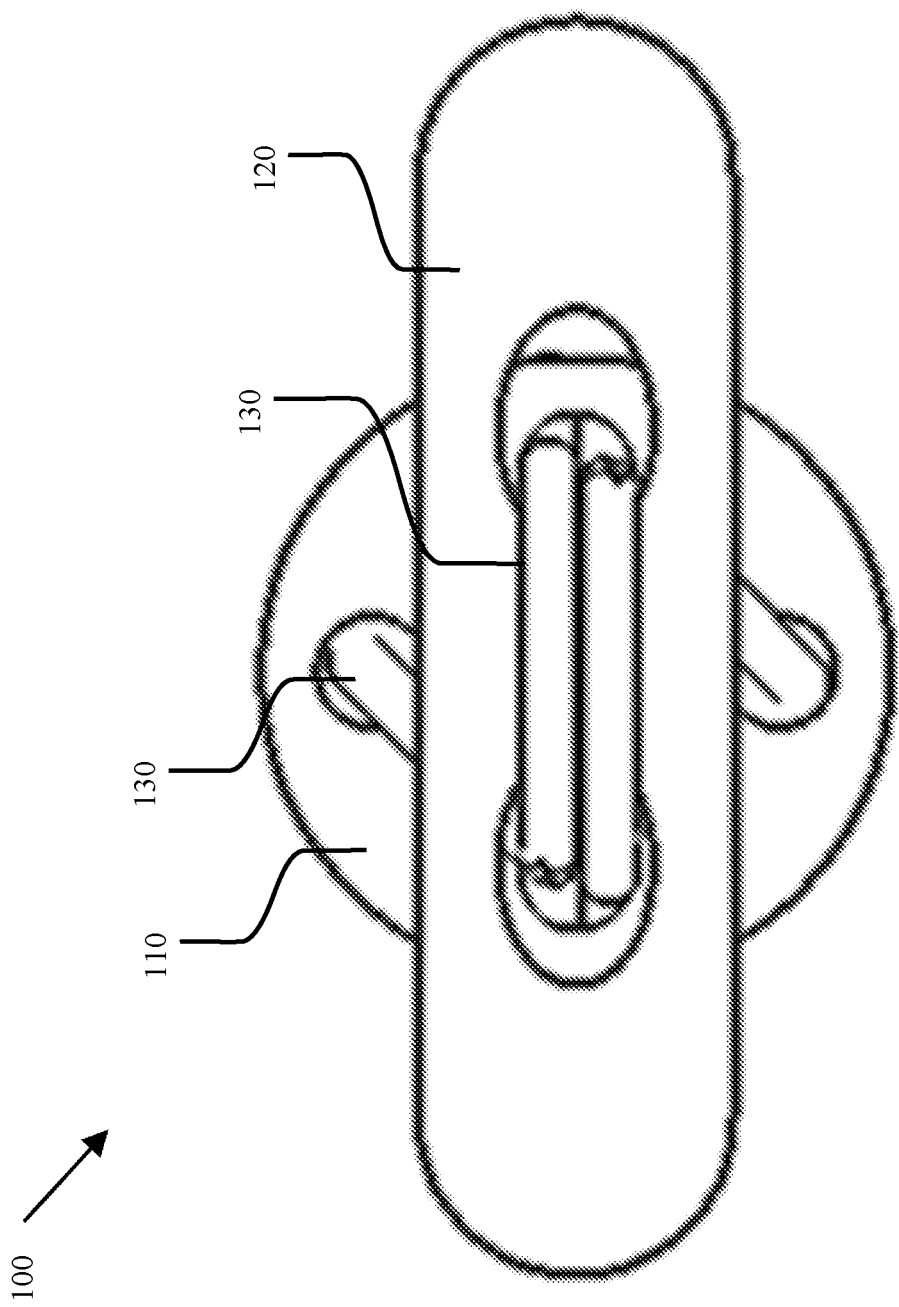
FIG. 4 shows a bottom-view illustration of an exemplary suture-button assembly, per an embodiment herein.

Per FIGS. 1, 2, and 3, for the second suture button assembly, each primary aperture 111 of the primary button has one suture strand 130 inserted therethrough. Alternatively, in some embodiments, each primary aperture 111 has two or more of the plurality of suture strands inserted therethrough. In some embodiments, each primary aperture 111 has 2, 3, 4, 5, 6 or more suture strands inserted therethrough. In some embodiments, each secondary aperture 121 has one or more of the plurality of suture strands inserted therethrough. Per FIGS. 1, 2 and 4, each secondary aperture 121 has two suture strands 130 inserted therethrough. As shown, each secondary aperture 121 has one suture strand 130 inserted distally and one suture strand 130 inserted proximally therethrough. Alternatively, each secondary aperture 121 has two suture strands 130 inserted distally therethrough. Alternatively, each secondary aperture 121 has two suture strands 130 inserted proximally therethrough. Alternatively, in some embodiments, each secondary aperture 121 has three or more sutures strands 130 inserted therethrough. In some embodiments, each secondary aperture 121 has 2, 3, 4, 5, 6 or more sutures strands 130 inserted therethrough.

Per FIG. 3, once the plurality of suture strands has been inserted through the apertures of the primary and secondary buttons, coupling the lock 140 to the primary button 110 prevents each of the plurality of suture strands 130 from translating through one or more of the plurality of primary apertures 111. In some embodiments, coupling the lock 140 to the primary threaded portion 141 prevents each of the plurality of suture strands 130 from translating through one or more of the plurality of primary apertures by compressing at least a portion of each of the plurality of suture strands 130 between the distal face 145 of the lock 140 and the primary button proximal face 113.

In some embodiments, rotating the lock 140 in a first direction relative to the primary button inserts the secondary threaded portion 141 of the lock 140 distally through the primary threaded portion 113 of the primary button 110, so as to compress at least a portion of each of the plurality of suture strands 130 located between the distal face 145 of the head 144 and the primary button proximal face 113. In some embodiments, rotating the lock 140 in a second direction relative to the primary button, opposite the first direction, translates the secondary threaded portion 141 of the lock 140 proximally through the primary threaded portion 113 of the primary button 110, so as to enable each of the plurality of suture strands 130 to translate through the plurality of primary apertures 111.

In some embodiments, per FIG. 8, at least a portion of the lock 140 extends beyond a distal face of the primary button 110 when the primary button 110 is coupled to the lock 140. In some embodiments, a distal face of the primary button 110 extends beyond a distal end of the secondary threaded portion 141 of the lock 140 when the primary button 110 is coupled to the lock 140. In some embodiments, at least a portion of the lock 140 extends beyond a distal face of the primary button 110 by an extension distance 147 of about 1 mm, 2 mm, 3 mm, 4 mm, 5 mm, 6 mm, 7 mm, 8 mm, 9 mm, 10 mm, or more when the primary button 110 is coupled to the lock 140. In some embodiments, a distal face of the primary button 110 extends beyond a distal end of the secondary threaded portion 141 of the lock 140 by an extension distance of about 1 mm, 2 mm, 3 mm, 4 mm, 5 mm, 6 mm, 7 mm, 8 mm, 9 mm, 10 mm, or more when the primary button 110 is coupled to the lock 140. In some embodiments, at least a portion of the lock 140 extends beyond a distal face of the primary button 110 into a bone or tissue. In some embodiments, at least a portion of the lock 140 extends beyond a distal face of the primary button 110 into a bone or tissue tunnel or hole. In some embodiments, at least a portion of the lock 140 extends beyond a distal face of the primary button 110 into a bone or tissue tunnel or hole when the primary button 110 is in contact with the bone or tissue tunnel.

Figure 13:
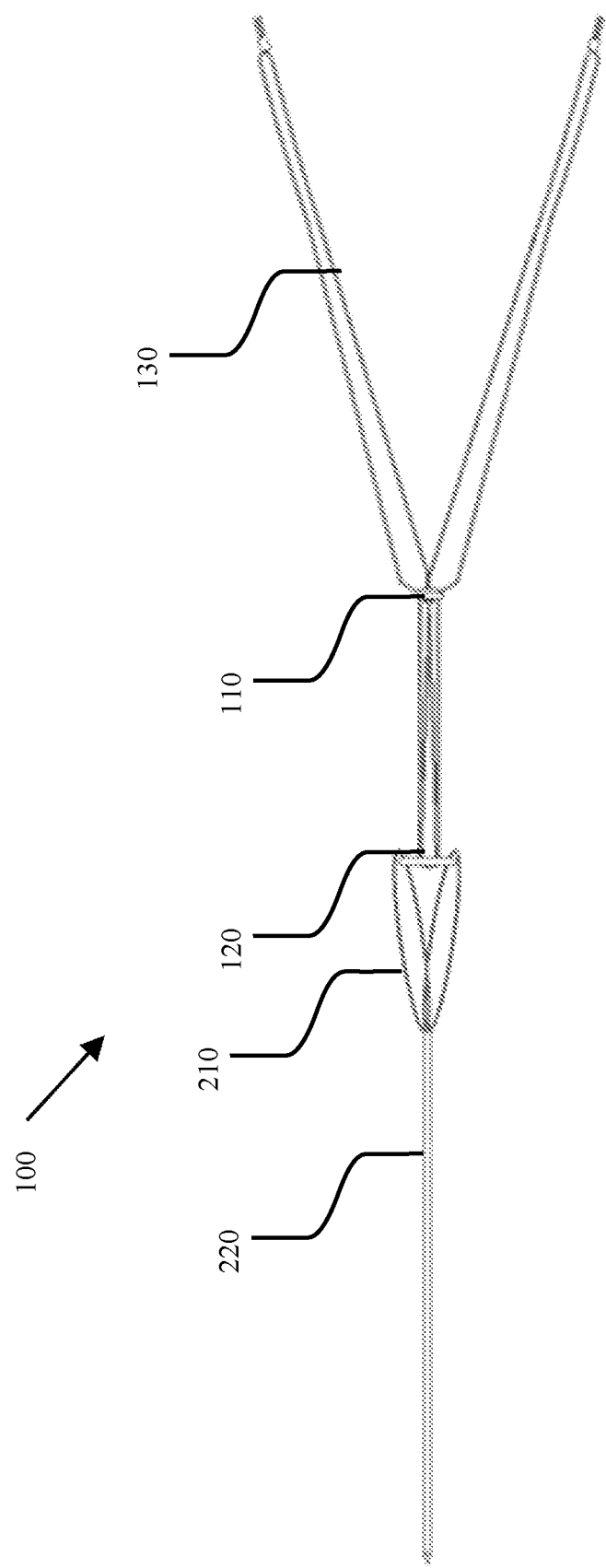
FIG. 13 shows a top-view illustration of an exemplary suture-button assembly with an insertion needle 220 device, per an embodiment herein.
Figures 14A, 14B:
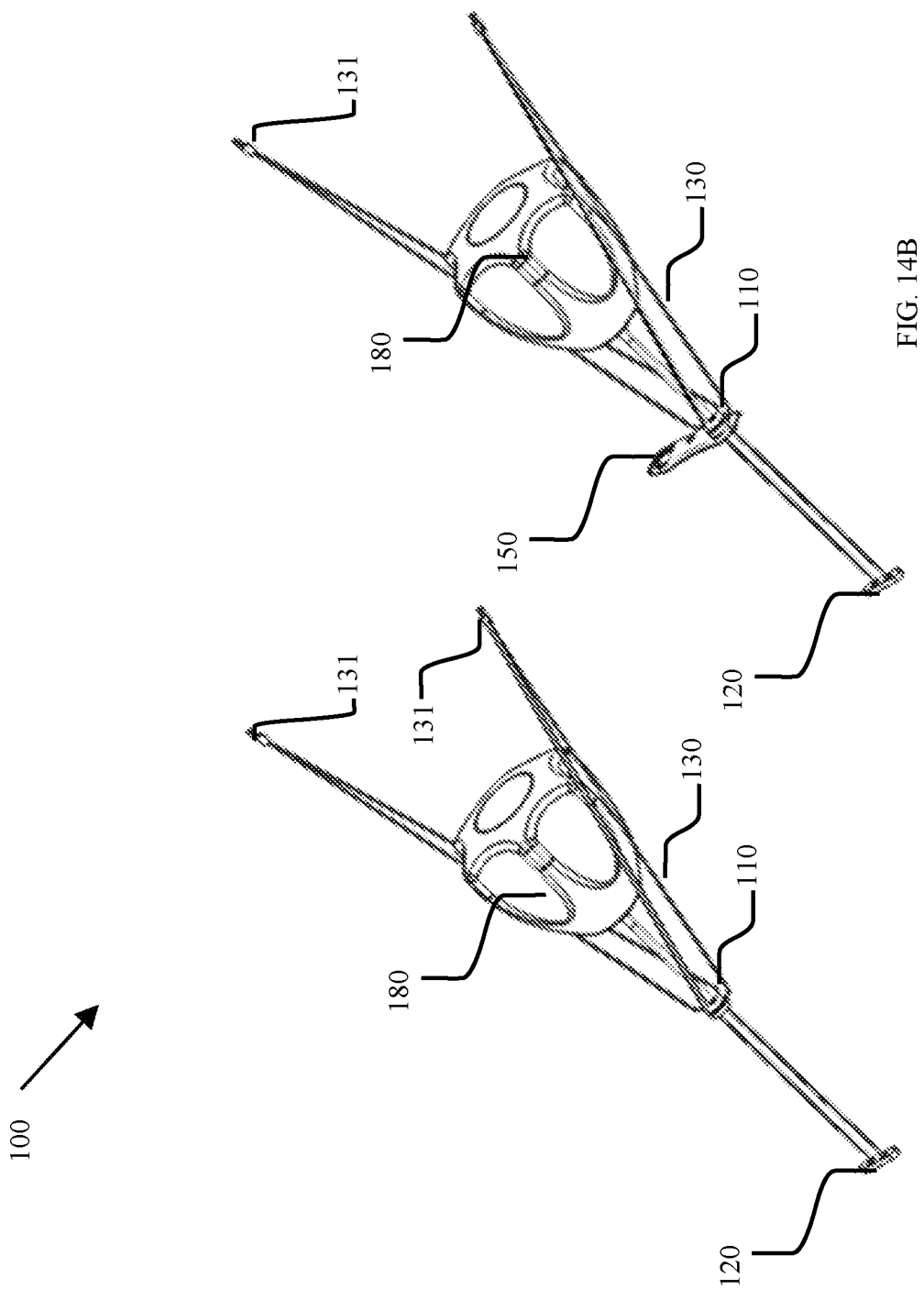
FIG. 14A shows a perspective illustration of an exemplary suture-button assembly with an exemplary lock driver, per an embodiment herein.
FIG. 14B shows a perspective illustration of an exemplary suture-button assembly with an exemplary lock driver and an exemplary insertion plate, per an embodiment herein.
Figure 15B:
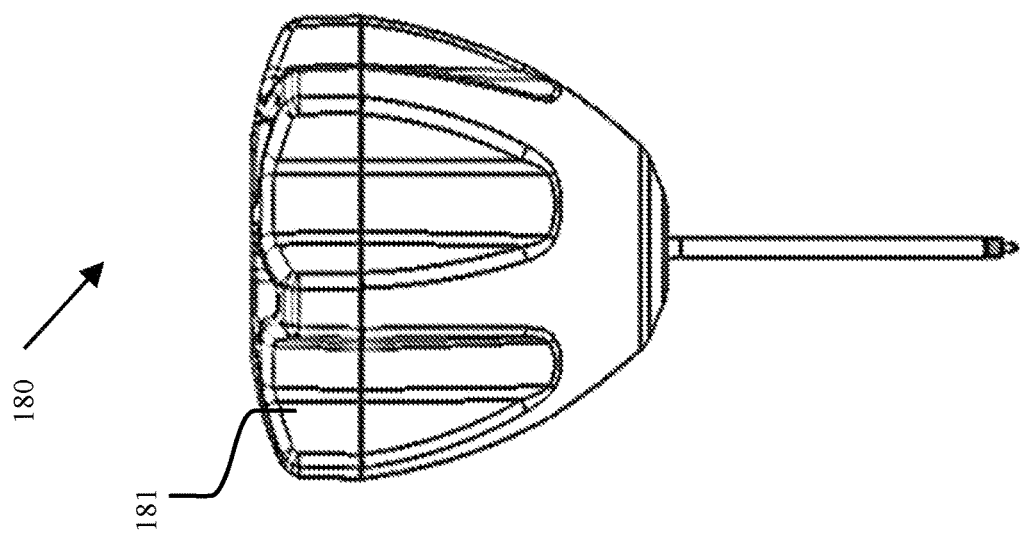
FIG. 15B shows a front-view illustration of an exemplary lock driver, per an embodiment herein.
Figure 15A:
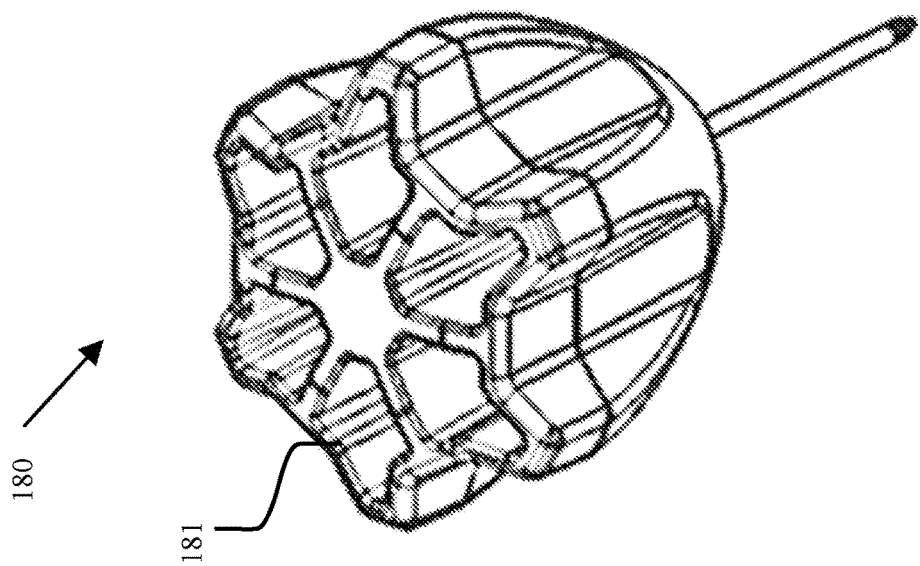
FIG. 15A shows a perspective illustration of an exemplary lock driver, per an embodiment herein.
Figure 16B:
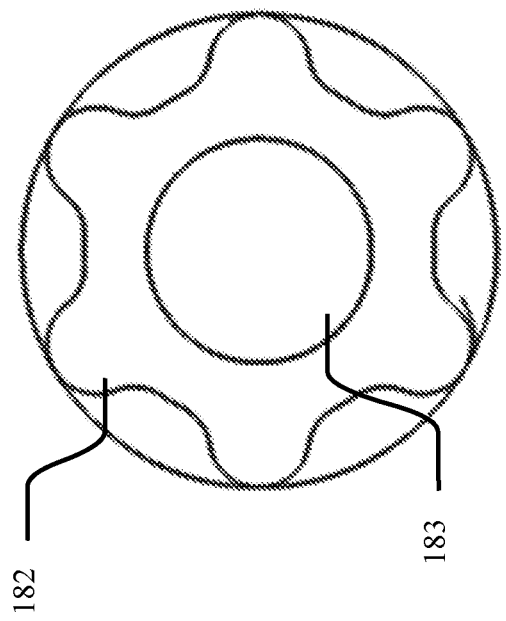
FIG. 16B shows a bottom-view illustration of an exemplary lock driver, per an embodiment.
Figure 16A:
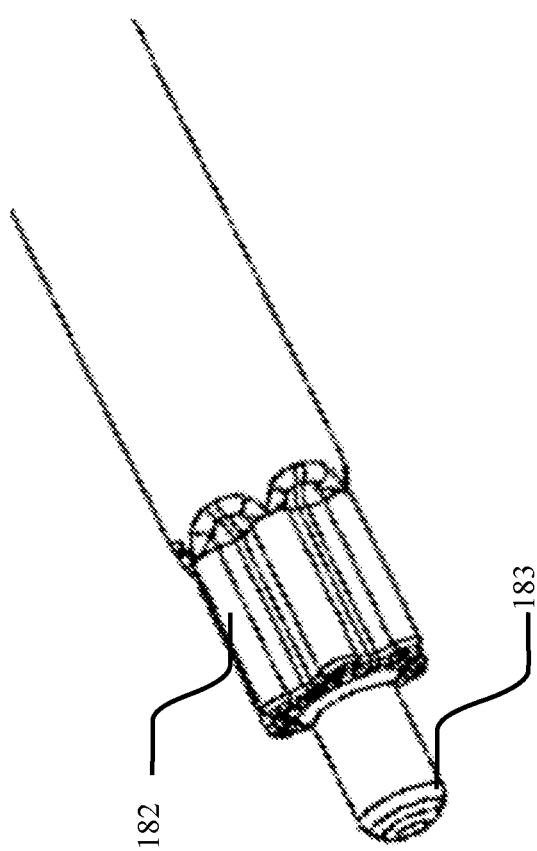
FIG. 16A shows a detailed perspective illustration of an exemplary lock driver, per an embodiment herein.
Figure 17A:
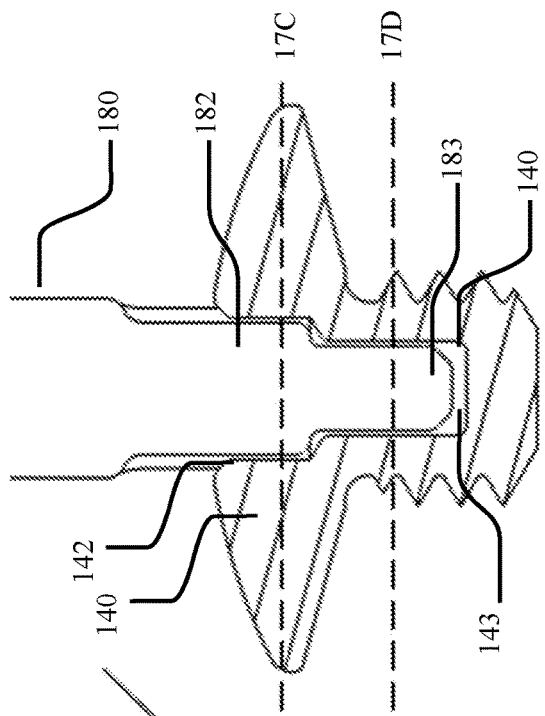
FIG. 17A shows a detailed perspective illustration of the driving feature of an exemplary lock driver rotating the lock, per an embodiment herein.
Figure 17B:
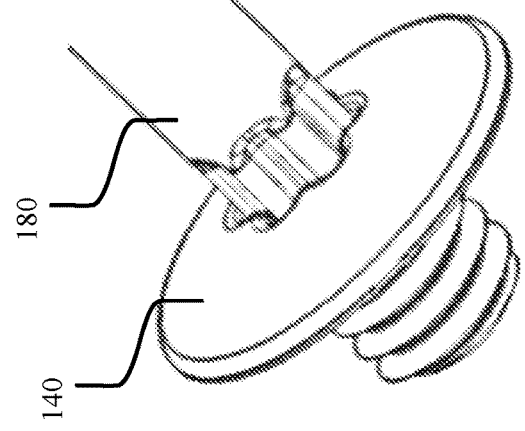
FIG. 17B shows a front cross-sectioned illustration of the driving feature and the aligning feature of an exemplary lock driver rotating the lock, per an embodiment herein.
Figure 17C:
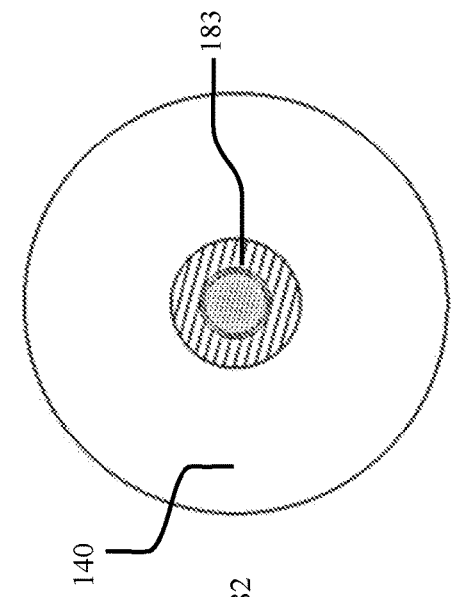
FIG. 17C shows a first front cross-sectional illustration of the driving feature and the aligning feature of an exemplary lock driver rotating the lock, per an embodiment herein.
Figure 17D:
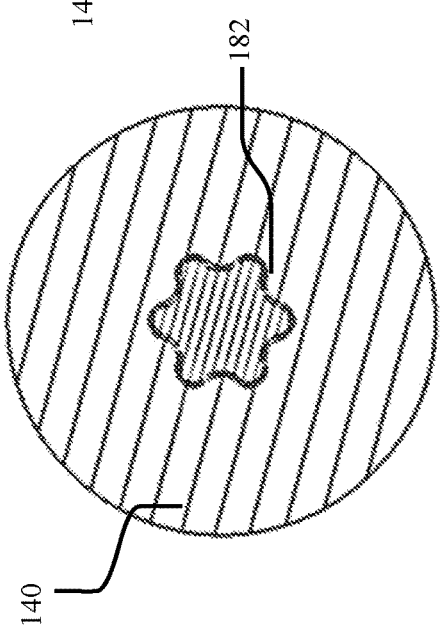
FIG. 17D shows a second front cross-sectioned illustration of the driving feature and the aligning feature of an exemplary lock driver rotating the lock, per an embodiment herein.
Figure 18:
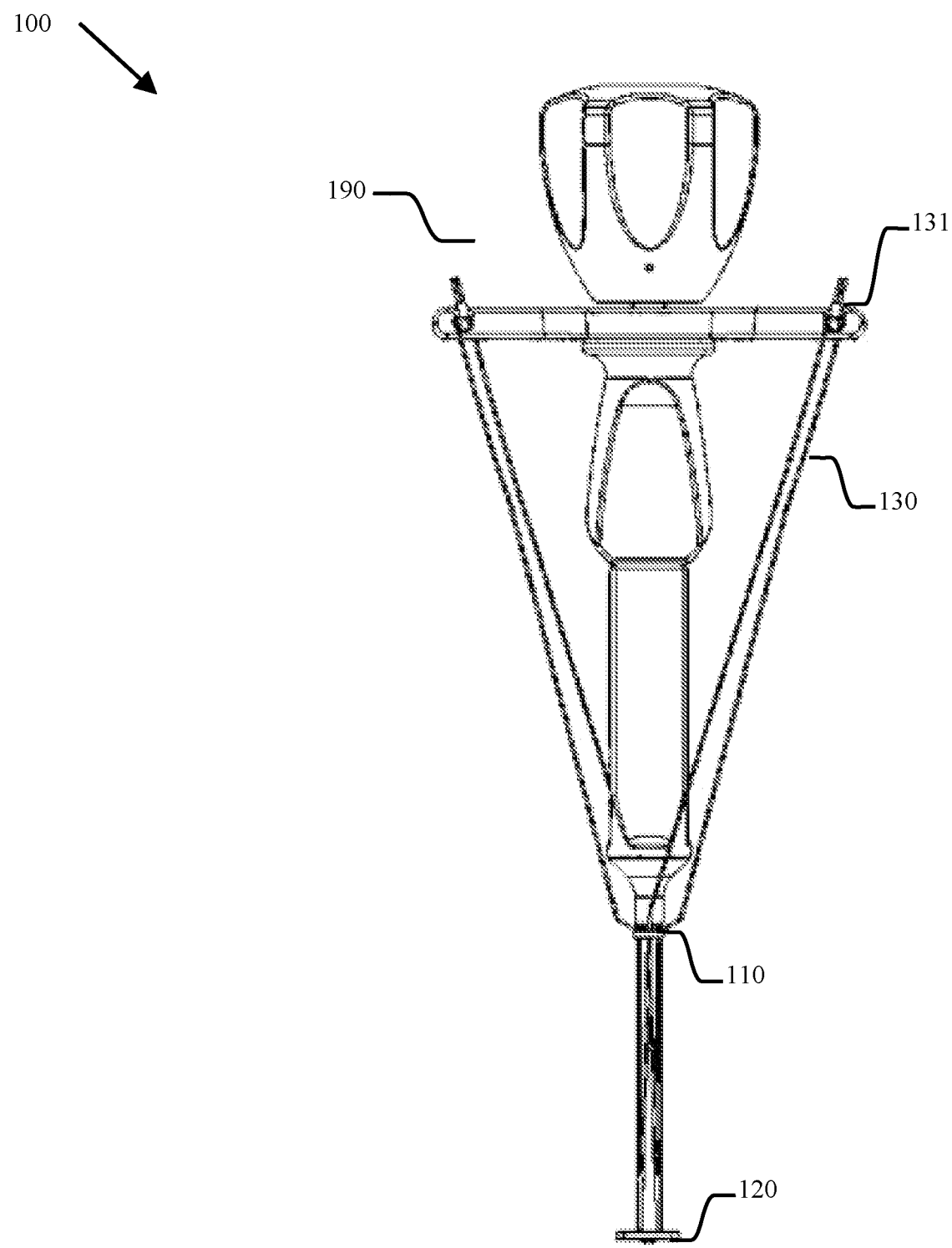
FIG. 18 shows a front-view illustration of an exemplary suture-button system having a tightening tool, per an embodiment.
Figures 19A, 19B, 19C:
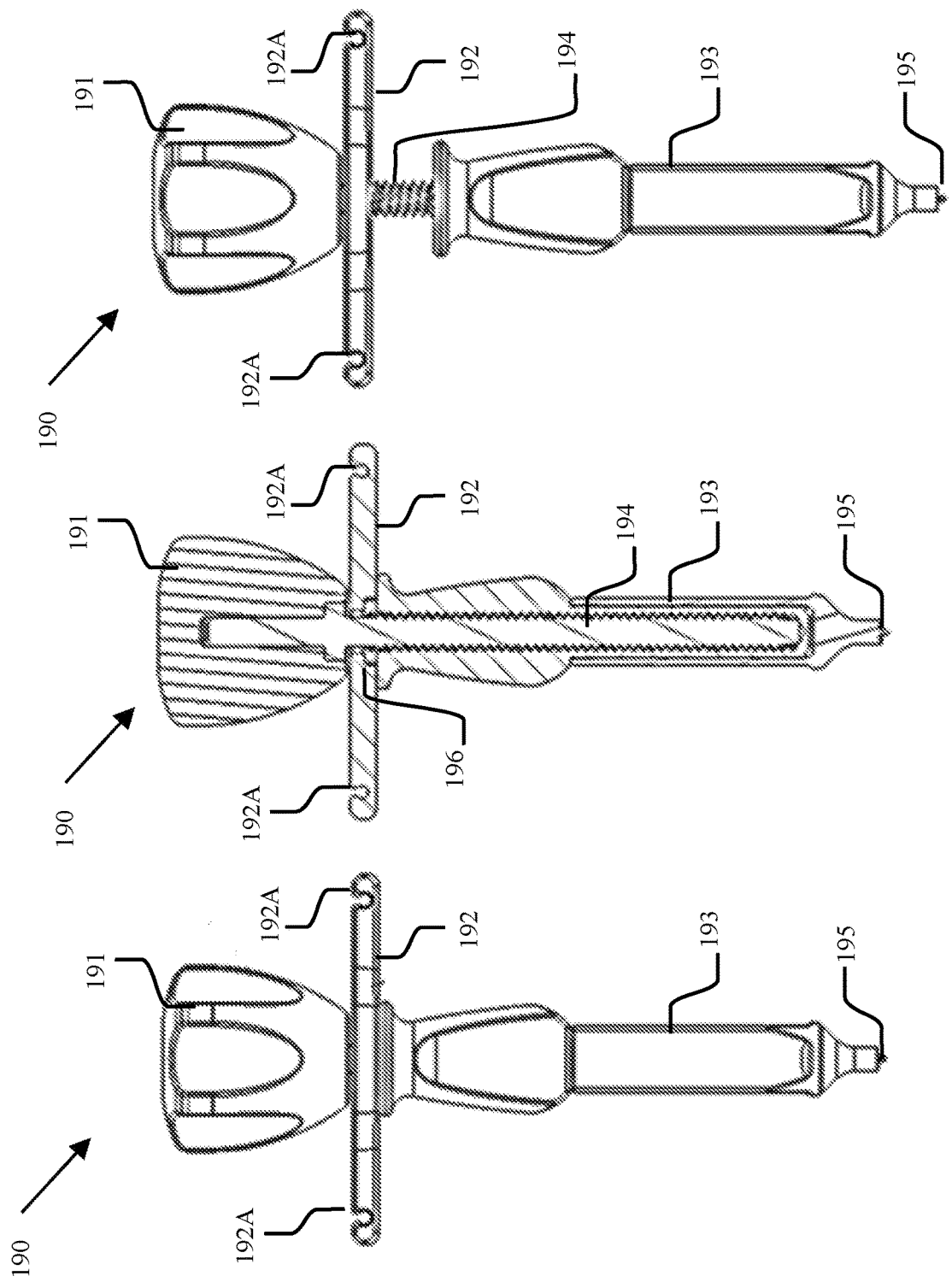
FIG. 19A shows a front-view illustration of an exemplary tightening tool in a collapsed position, per an embodiment herein.
FIG. 19B shows a front cross-sectioned illustration of an exemplary tightening tool in the collapsed position, per an embodiment herein.
FIG. 19C shows a front-view illustration of an exemplary tightening tool in an expanded position, per an embodiment herein.
Figure 20:
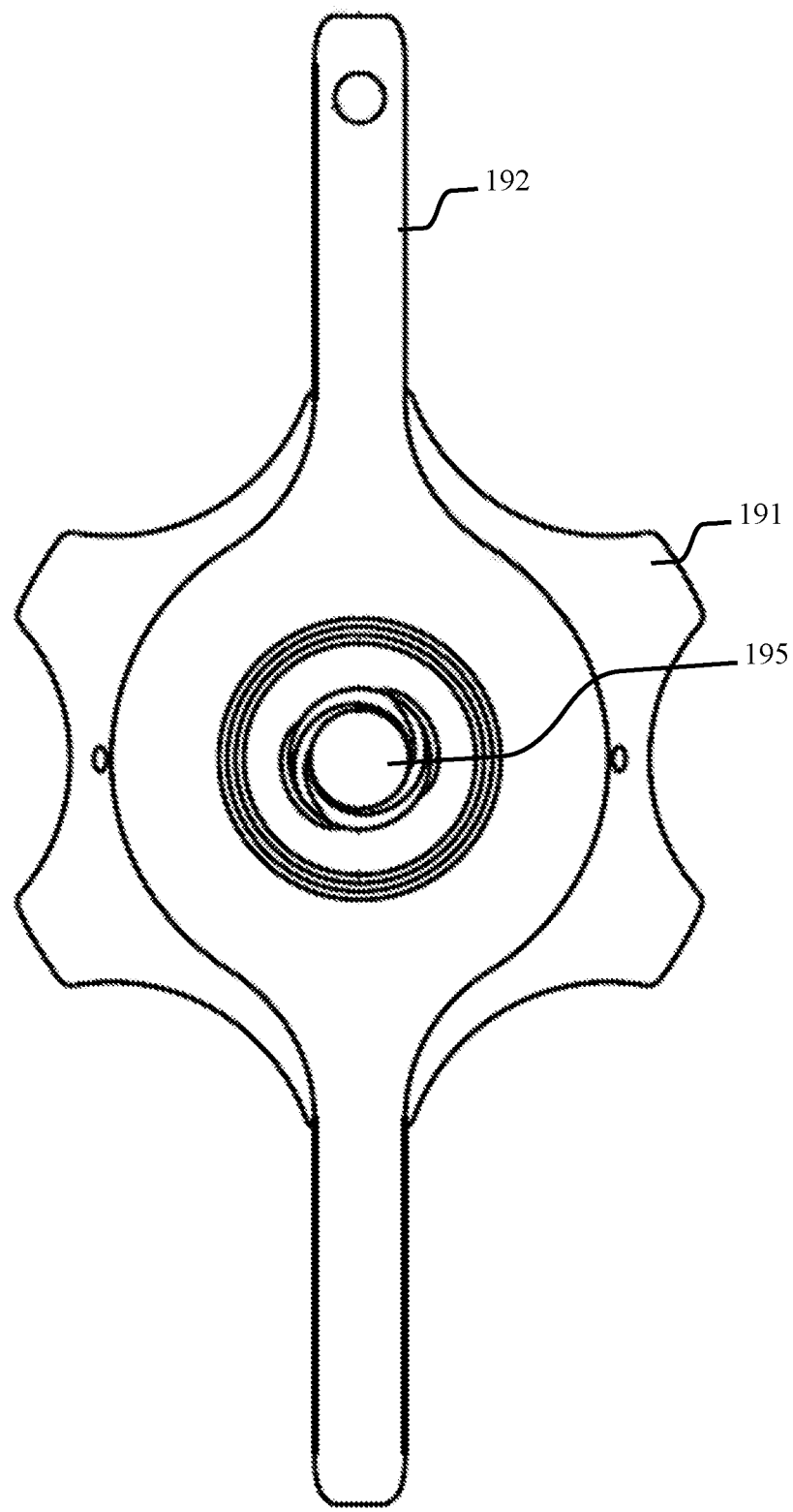
FIG. 20 shows a top-view illustration of an exemplary tightening tool, per an embodiment herein.
Figure 21:
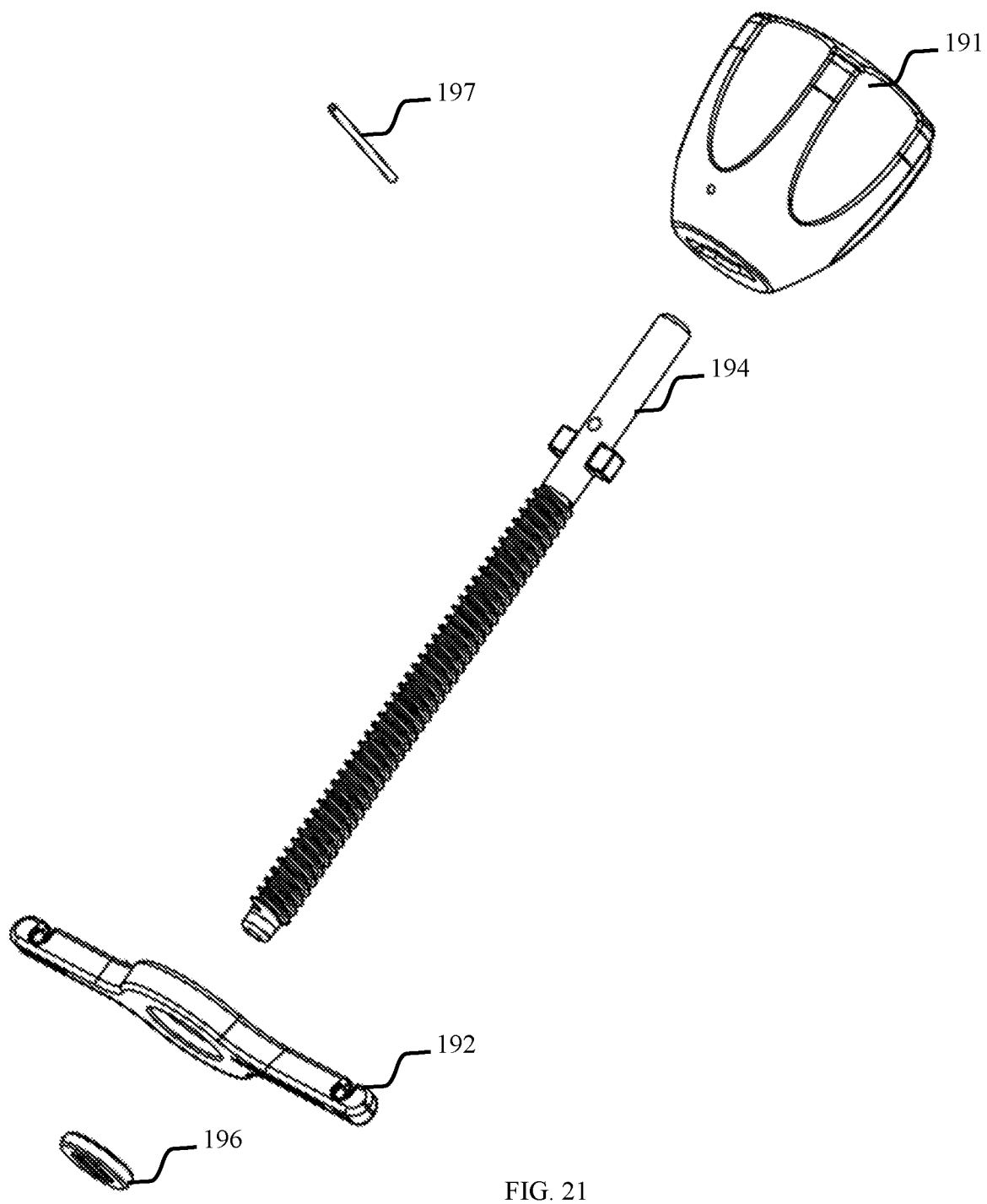
FIG. 21 shows a perspective exploded illustration of an exemplary tightening tool, per an embodiment herein.
Figure 22:
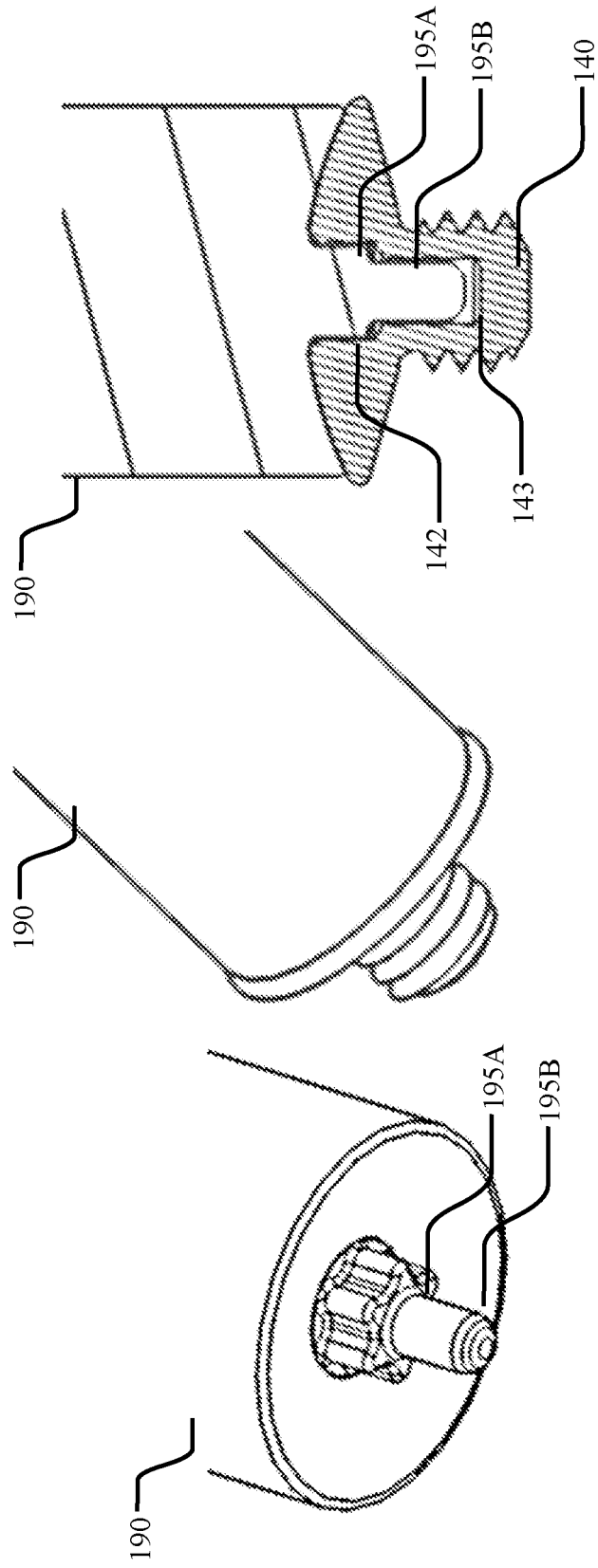
FIG. 22A shows a detailed bottom-left-front perspective illustration of a tensioning feature and an alignment feature of an exemplary tightening tool, per an embodiment herein.
FIG. 22B shows a detailed top-right-front illustration of an exemplary tightening tool engaged with an exemplary lock, per an embodiment herein.
FIG. 22C shows a cross-section illustration of an exemplary tightening tool engaging with the lock, per an embodiment herein.
Figure 23:
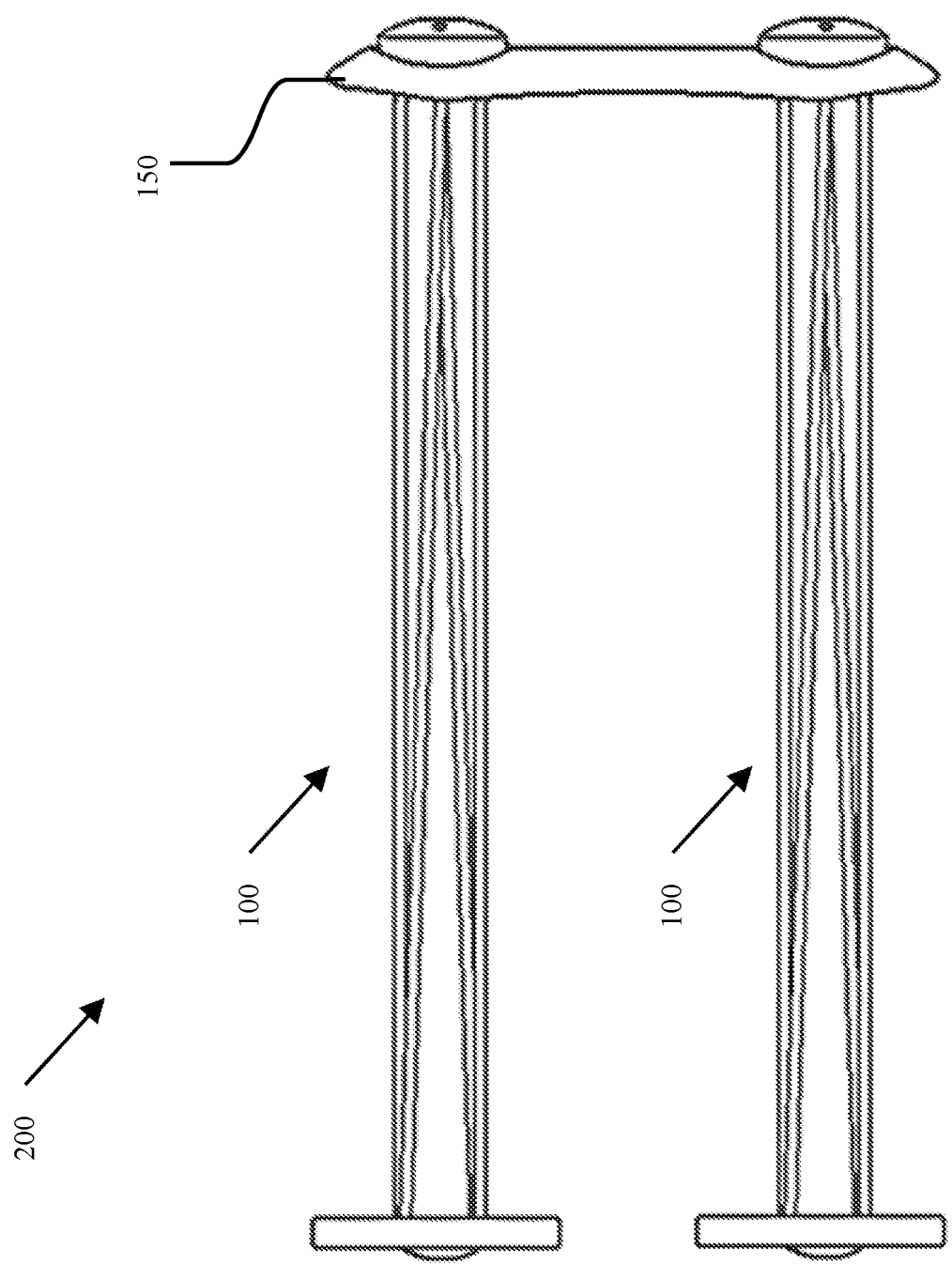
FIG. 23 shows a front-view illustration of an exemplary suture-button assembly comprising two suture-button systems and an insertion plate, per an embodiment herein.
Figure 24:
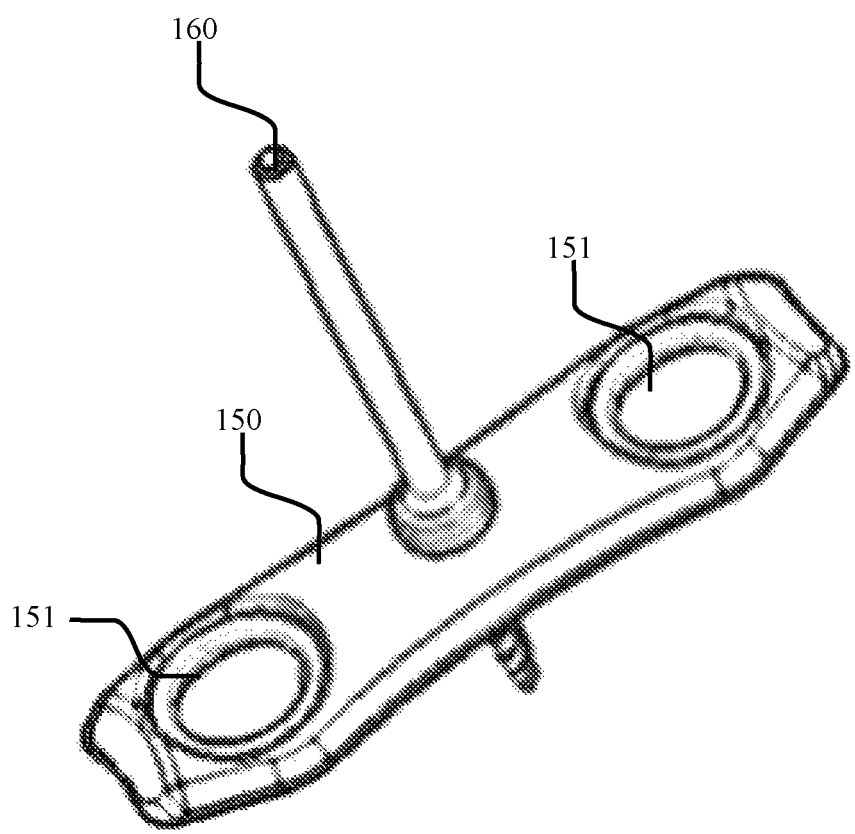
FIG. 24 shows a perspective illustration of an exemplary insertion plate coupled to an exemplary insertion screw, per an embodiment herein.
Figure 28A:
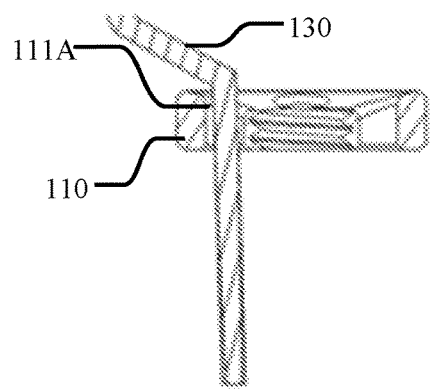
FIG. 28A shows a cross-section illustration of inserting a suture strand through a first primary aperture of the primary button, per an embodiment herein.
Figure 28B:
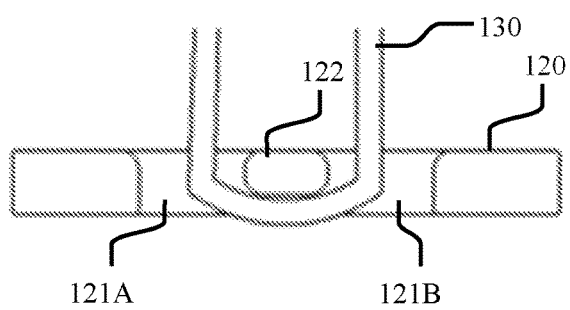
FIG. 28B shows a perspective illustration of inserting a suture strand through a first secondary aperture and a second secondary aperture of the secondary button, per an embodiment herein.
Figure 28C:
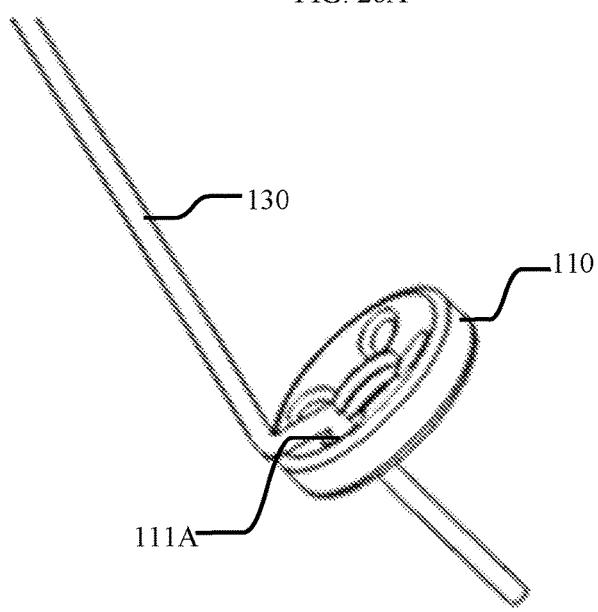
FIG. 28C shows a perspective illustration of inserting a suture strand through a first primary aperture of the primary button, per an embodiment herein.
Figure 28D:
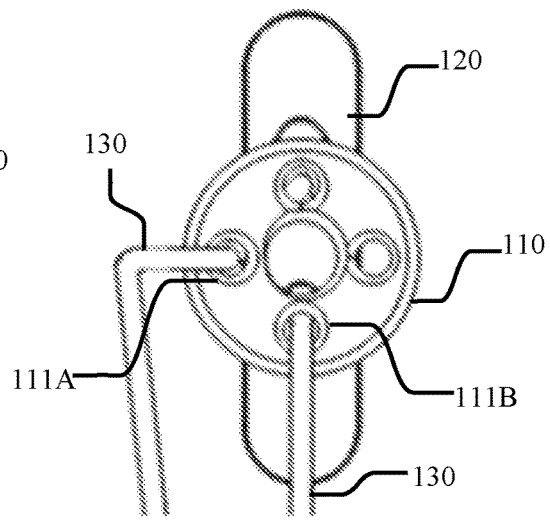
FIG. 28D shows a perspective illustration of inserting a suture strand through a second primary aperture of the primary button, per an embodiment herein.

In some embodiments, per FIG. 13, the system 100 further comprises an insertion suture 210, an insertion needle 220, or both. In some embodiments, the secondary button 120 is attached to the insertion needle 220 via an insertion suture 210. In some embodiments, the insertion needle 220 is configured to be inserted through a hole in a targeted tissue, which then pulls the secondary button 120 therethrough via the insertion suture 210. In some embodiments, pulling the secondary button 120 through the hole in the targeted tissue also pulls the one or more suture strands 130 that is coupled to the secondary button through said hole. In some embodiments, the insertion needle 220 is then disconnected from the secondary button 120 by cutting and removing the insertion suture 210.

In some embodiments, per FIGS. 14A-17D, the system 100 further comprises a lock driver device 180. In some embodiments, the lock driver 180 comprises a driving feature 182 that is configured to rotate the lock 140 relative to the primary button 110. In some embodiments, the driving feature 182 is a male driving feature wherein the driver feature 142 of the lock 140 is a female driver feature. In some embodiments, the driving feature 182 is a female driving feature wherein the driver feature 142 of the lock 140 is a male driver feature. In some embodiments, at least a portion of the driver feature 142 fits within a portion of the driving feature 182. In some embodiments, at least a portion of the driving feature 182 fits within a portion of the driver feature 142. In some embodiments, the lock driver 180 further comprises an aligning feature 183 configured to align the lock driver 180 to the alignment feature 143 of the lock 140. In some embodiments, the aligning feature 183 is configured to align the lock driver 180 to the alignment feature 143 of the lock 140 while the lock driver 180 rotates the lock 140 relative to the primary button 110. In some embodiments, rotating the lock driver 180 in a first direction inserts the secondary threaded portion 141 of the lock 140 distally through the primary threaded portion 113 of the primary button 110. In some embodiments, rotating the lock driver 180 in a second direction opposite the first direction translates the secondary threaded portion 141 of the lock 140 proximally through the primary threaded portion 113 of the primary button 110. In some embodiments, the alignment feature 183 is distal to the driving feature 182. In some embodiments, a maximum outer diameter of the alignment feature 183 is less than a maximum outer diameter of the driving feature 182. As shown, the driver feature 142 comprise a torx driver feature, Alternatively, in some embodiments, the driver feature 142 comprises a Philips driver feature 142, a flathead driver feature 142, a hex driver feature 142, or a square socket feature. In some embodiments, the lock driver 180 enables a greater tightening force than can be applied by hand. In some embodiments, the lock driver 180 enables a more precise and tunable tightening force than can be applied by hand.

In some embodiments, per FIGS. 18-22C, the system 100 further comprises a tightening tool 190. In some embodiments, the tightening tool 190 comprises: a threaded rod 194; a knob 191; a spinner 192, a collar 196, and a handle 193. In some embodiments, the knob 191 is coupled to the threaded rod 194. In some embodiments, the knob 191 is permanently coupled to the threaded rod 194. In some embodiments, the knob 191 is removably coupled to the threaded rod 194. In some embodiments, the knob 191 is coupled to a proximal end of the threaded rod 194. In some embodiments, the collar 196 is coupled to the threaded rod 194. In some embodiments, the collar 196 is coupled to the threaded rod 194 by a fastener, an adhesive, a pin 197, welding or any combination thereof. In some embodiments, the spinner 192 is positioned between the knob 191 and the collar 196. In some embodiments, the spinner 192 comprises an aperture accepting the threaded rod 194. In some embodiments, the spinner 192 further comprises a terminator channel 192A accepting the coupled ends of one or more suture strands 130. In some embodiments, the spinner 192 further comprises a terminator channel 192A accepting the terminator of the suture strand 130. In some embodiments, the spinner 192 comprises 1, 2, 3, 4, 5, 6, or more terminator channels 192A. In some embodiments, the handle 193 comprises a cavity, wherein at least a portion of the cavity comprises a threaded feature configured to couple to the threaded rod 194. In some embodiments, a distal portion of the handle 193 comprises a tensioning feature 195A configured to rotate the driver feature of the lock 140. In some embodiments, the knob 191 is coupled to the proximal end of the threaded rod 194 by a pin 197, an adhesive, a fastener, a press-fit, a weld, or any combination thereof. As shown, the collar 196 is coupled to the threaded rod 194 by a fastener. Alternatively, in some embodiments, the collar 196 is coupled to the threaded rod 194 by a pin, an adhesive, a press-fit, a weld, or any combination thereof. In some embodiments, the lock 140 further comprises the alignment feature 143, and wherein the distal portion of the handle 193 further comprises a tensioning alignment feature 195B that couples to the alignment feature 143. In some embodiments, rotating the knob 191 and the threaded rod 194 in a first direction with respect with to the handle 193 translates the knob 191 and the spinner distally with respect to the handle 193. In some embodiments, rotating the knob 191 and the threaded rod 194 in a second direction opposite the first direction translates the knob 191 and the spinner proximally with respect to the handle 193. In some embodiments, the knob 191 is rotated to translate the spinner 192 proximally or distally, so as to obtain a desired tension of suture strands 130 that are coupled to a terminator channel 192A. In some embodiments, rotating the handle 193 in a first direction inserts the secondary threaded portion 141 of the lock 140 distally through the primary threaded portion 113 of the primary button 110. In some embodiments, rotating the handle 193 in a second direction opposite the first direction translates the secondary threaded portion 141 of the lock 140 proximally through the primary threaded portion 113 of the primary button 110. In some embodiments, the tightening tool 190 enables a greater tightening force than can be applied by hand. In some embodiments, the tightening tool 190 enables a more precise and tunable tightening force than can be applied by hand.

In some embodiments, applying tension between two ends of each of the one or more suture strands 130 reduces a distance between the primary button 110 and the secondary button 120. In some embodiments, applying tension between two ends of each of the one or more suture strands 130 reduces a distance between the distal surface of the primary button 110 and a proximal surface of the secondary button 110. In some embodiments, applying tension between two ends of each of the one or more suture strands 130 provides a clamping force between the distal surface of the primary button 110 and a proximal surface of the secondary button 110. In some embodiments, applying tension between two ends of each of the one or more suture strands 130 increases a clamping pressure that the primary button 110 and the secondary button 110 apply to a target tissue therebetween. In some embodiments, applying tension between two ends of each of the one or more suture strands 130 increases a clamping pressure that the distal surface of the primary button 110 and the proximal surface secondary button 110 apply to a target tissue therebetween.

In some embodiments, the target tissue comprises two or more portions of a bone, a muscle tissue, an epithelial tissue, a connective, tissue, a nervous tissue, or any combination thereof. In some embodiments, two or more of the following are clamped together between the primary button 110 and the secondary button 110: a bone, a muscle tissue, an epithelial tissue, a connective, tissue, a nervous tissue, or any combination thereof. In some embodiments, upon tensioning of the suture strands 130, the primary button 110 and the secondary button 120 clamp a bone to: another bone, a muscle tissue, an epithelial tissue, a connective, tissue, a nervous tissue, or any combination thereof. In some embodiments, upon tensioning of the suture strands 130, the primary button 110 and the secondary button 120 clamp a muscle tissue to: bone, another muscle tissue, an epithelial tissue, a connective, tissue, a nervous tissue, or any combination thereof. In some embodiments, upon tensioning of the suture strands 130, the primary button 110 and the secondary button 120 clamp an epithelial tissue to: bone, muscle tissue, another epithelial tissue, a connective, tissue, a nervous tissue, or any combination thereof. In some embodiments, upon tensioning of the suture strands 130, the primary button 110 and the secondary button 120 clamp a connective tissue to: bone, muscle tissue, epithelial tissue, another connective, tissue, a nervous tissue, or any combination thereof. In some embodiments, upon tensioning of the suture strands 130, the primary button 110 and the secondary button 120 clamp a nervous tissue to: bone, muscle tissue, epithelial tissue, connective, tissue, another nervous tissue, or any combination thereof.

Suture-Button Assemblies

Another aspect provided herein, per FIGS. 23-26B, is a suture-button assembly 200 comprising two suture-button systems 100 and an insertion plate 150. In some embodiments, the suture button assembly 200 comprises 2, 3, 4, 5, 6, or more suture button systems 100. As shown, the insertion plate 150 comprises two insertion plate apertures 151, wherein each insertion plate aperture 151 accepts at least one suture strand. Alternatively, in some embodiments, each insertion plate apertures 151 accepts the sutures of 1, 2, 3, 4, 5, 6 or more suture button assemblies. In some embodiments, the plurality of insertion plate apertures 151 comprises 2, 3, 4, 5, 6, or more insertion plate apertures 151, wherein each insertion plate aperture 151 accepts the sutures of one suture button assembly. In some embodiments, each insertion plate apertures 151 accepts 1, 2, 3, 4, 5, 6 or more sutures. In some embodiments, the plurality of insertion plate apertures 151 In some embodiments, a screw hole 152 is positioned between two of the plurality of insertion plate apertures 151. In some embodiments, the screw hole 152 is positioned equidistant between two of the plurality of insertion plate apertures 151.

In some embodiments, the assembly further comprises an insertion screw 160. In some embodiments, insertion screw 160 is configured to be removably coupled with the screw hole 152. In some embodiments, the insertion screw 160 comprises a first portion 161, a second portion 162 configured to attach to a bone of a patient, and a third portion 163 having length and/or diameter greater than a greatest length or diameter of the screw hole 152. In some embodiments, the third portion 163 prevents the first portion 161 from passing through the screw hole 152 after the second portion 162 has been inserted therethrough. In some embodiments, the second portion comprises a threaded feature configured to attach to the bone of the patient.

Method of Assembling a First Suture button System

Another aspect provided herein is a method of assembling a first suture button system 100. In some embodiments, the method comprises: providing a first suture-button system 100 wherein the primary button 110 comprises a first primary aperture 111 and a second primary aperture 111, wherein the secondary button 120 comprises a first secondary aperture 121 and a second secondary aperture 121, and wherein the first suture button system comprises one suture strand 130. In some embodiments, the method comprises inserting the suture strand 130 through the first primary aperture 111, inserting the one suture strand 130 through the first secondary aperture 121, inserting the one suture strand 130 through the second secondary aperture 121, and inserting the one suture strand 130 through the second primary aperture 111. In some embodiments, one or more of the steps of inserting the suture strand 130 through the first primary aperture 111, through the first secondary aperture 121, through the second secondary aperture 121, and through the second primary aperture 111 are performed simultaneously. In some embodiments, the method further comprises coupling the two ends of the suture strand 130 together. In some embodiments, the method further comprises coupling the two ends of the suture strand 130 by tying the two ends of the suture strand 130 together. In some embodiments, the method further comprises coupling the two ends of the suture strand 130 with a terminator.

In some embodiments, the method further comprises inserting the secondary button 120 through a hole in a proximal surface of a bone or tissue of a patient, and tightening the suture such that the primary button 110 and the secondary button 120 are tightly pressed against opposing surfaces of the bone. In some embodiments, the secondary button 120 is inserted through a bone or tissue hole extending through at least one bone. In some embodiments, the bone or tissue hole is a tunnel, channel, passageway, or any combination thereof. In some embodiments, the secondary button 120 is attached to an insertion needle 220 via one or more insertion suture 210 loops. In some embodiments, the insertion suture 210 loops may be formed by passing an insertion suture 210 through one or more secondary apertures 121 in the secondary button 120 and attaching both free ends of the one or more insertion suture strands 210 to the insertion needle 220. In some embodiments, the free ends of the one or more insertion suture strands 210 are attached to the insertion needle 220 via crimping. In some embodiments, the insertion needle 220 may be inserted through said bone or tissue hole on a first side of the bone or tissue, and received on a second side, such that the secondary button 120 is pulled through the hole in its most narrow configuration. In some embodiments, the secondary button 120, after passing through the bone or tissue hole in its most narrow configuration, is then pivoted such that it lies flat against the bone or tissue. In some embodiments, the secondary button 120 lies against the bone or tissue on its length 120A. In some embodiments, the primary button 110 and secondary button 120 are disposed on either side of the bone or tissue hole with the suture 130 extending through the bone or tissue hole. In some embodiments, the insertion needle 220 is disconnected from the secondary button by cutting and removing the insertion suture 210. In some embodiments, the suture strand 130 is tightened, such that the primary and secondary buttons apply a clamping force or pressure on a first and second side of a bone or tissue.

As described herein, tightening the suture includes applying a tension to the coupled ends of the suture 130. In some embodiments, pulling the coupled ends of the suture 130 applies tension to the suture. In some embodiments, pulling the coupled ends of the suture 130 in a proximal direction applies tension to the suture. In some embodiments, the tightening is performed by hand. In some embodiments, the tightening is performed by the lock driver described herein. In some embodiments, the tightening is performed by rotating the tightening tool 190 herein. In some embodiments, the tightening comprises inserting the suture strand loop 130 within the terminator channels 192A of the spinner 192, coupling the tensioning feature 195A and the driver feature of the lock 140, and rotating the knob 191 with respect to the handle 193. In some embodiments, the tightening comprises inserting the suture strand loop 130 within the terminator channels 192A of the spinner 192, coupling the tensioning feature 195A and the driver feature of the lock 140, rotating the knob 191 with respect to the handle 193, and rotating the tightening tool 190 with respect to the driving feature of the lock 140. In some embodiments, rotating the knob 191 in a first direction translates the spinner 192 and terminator channels 192A proximally from the handle 193, thereby tightening the suture strand 130. In some embodiments, rotating the knob 191 in a second direction translates the spinner 192 and terminator channels 192A distally to the handle 193, thereby loosening the suture strand 130, and decreasing the tension. In some embodiments, once the desired tension is reached the lock 140 is tightened against the primary button 110 such that the suture is locked in place therebetween. In some embodiments, the lock 140 is loosened against the primary button 110 to enable readjustment of the tension of the suture strand, wherein the lock 140 is subsequently tightened against the primary button 110 once the desired tension is reached. In some embodiments, the method further comprises trimming the loose ends of the suture.

Method of Assembling a Second Suture Button System

Further provided herein, per FIGS. 27A-29B, is a method of assembling a second suture button system 100. In some embodiments, the method comprises providing a second suture-button system 100 wherein the primary button 110 comprises a first primary aperture 111, a second primary aperture 111, a third primary aperture 111, and a fourth primary aperture 111, the secondary button 120 comprises a first secondary aperture 121 and a second secondary aperture 121, and the one or more a suture strands 130 consists of a first suture strand 130 and a second suture strand 130.

In some embodiments, the method comprises: inserting the first suture strand 130 through the first primary aperture 111; inserting the first suture strand 130 through the first secondary aperture 121; inserting the first suture strand 130 through the second secondary aperture 121; inserting the first suture strand 130 through the second primary aperture 111; inserting the second suture strand 130 through the third primary aperture 111; inserting the second suture strand 130 through the first secondary aperture 121; inserting the second suture strand 130 through the second secondary aperture 121; and inserting the second suture strand 130 through the fourth primary aperture 111. In some embodiments, one or more of the inserting the first suture strand 130 through the first primary aperture 111, inserting the first suture strand 130 through the first secondary aperture 121, inserting the first suture strand 130 through the second secondary aperture 121, inserting the first suture strand 130 through the second primary aperture 111, inserting the second suture strand 130 through the third primary aperture 111, inserting the second suture strand 130 through the first secondary aperture 121, inserting the second suture strand 130 through the second secondary aperture 121, and inserting the second suture strand 130 through the fourth primary aperture 111 are performed simultaneously.

In some embodiments, the method comprises: inserting the first suture strand 130 through the first primary aperture 111; inserting the first suture strand 130 through the first secondary aperture 121; inserting the first suture strand 130 through the second secondary aperture 121; inserting the first suture strand 130 through the second primary aperture 111; inserting the second suture strand 130 through the third primary aperture 111; inserting the second suture strand 130 through the second secondary aperture 121; inserting the second suture strand 130 through the first secondary aperture 121; and inserting the second suture strand 130 through the fourth primary aperture 111. In some embodiments, one or more of the inserting the first suture strand 130 through the first primary aperture 111, inserting the first suture strand 130 through the first secondary aperture 121, inserting the first suture strand 130 through the second secondary aperture 121, inserting the first suture strand 130 through the second primary aperture 111, inserting the second suture strand 130 through the third primary aperture 111, inserting the second suture strand 130 through the second secondary aperture 121, inserting the second suture strand 130 through the first secondary aperture 121, and inserting the second suture strand 130 through the fourth primary aperture 111 are performed simultaneously.

Figure 29A:
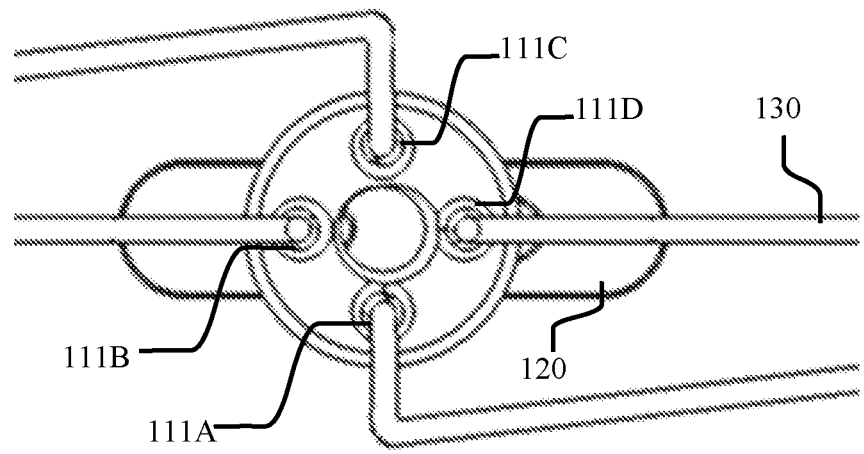
FIG. 29A shows a cross-section illustration of inserting a first and second suture strand through the respective apertures of the primary button, per an embodiment herein.
Figure 29B:
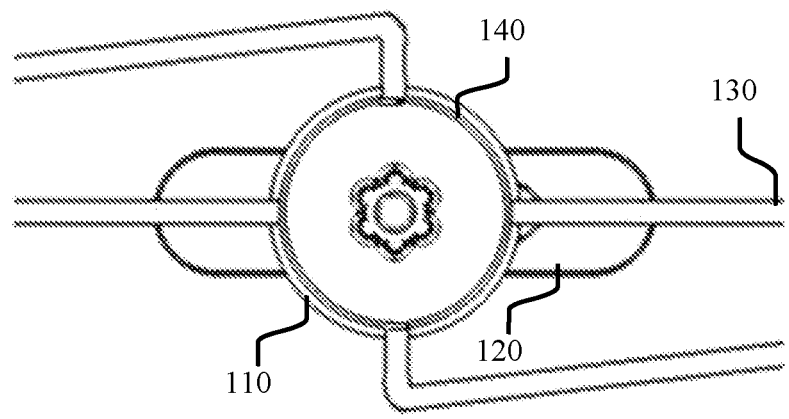
FIG. 29B shows a perspective illustration of a lock securing a first and second suture strand inserted through the respective apertures of the primary button, per an embodiment herein.

Per FIG. 29A, both the first primary aperture 111 and the third primary aperture 111 are adjacent to the second primary aperture 111 and the fourth primary aperture 111. Further as shown, the first primary aperture 111, the second primary aperture 111, the third primary aperture 111 and the fourth primary aperture 111 are arrayed sequentially in a clockwise direction about the primary button 110. Alternatively, in some embodiments, both the first primary aperture 111 and the second primary aperture 111 are adjacent to the third primary aperture 111 and the fourth primary aperture 111. In some embodiments, the first primary aperture 111, the third primary aperture 111, the second primary aperture 111 and the fourth primary aperture 111 are arrayed sequentially in a clockwise direction about the primary button 110. In some embodiments, the first primary aperture 111, the third primary aperture 111, the second primary aperture 111 and the fourth primary aperture 111 are arrayed sequentially in a counter-clockwise direction about the primary button 110. In some embodiments, the first primary aperture 111, the second primary aperture 111, the third primary aperture 111 and the fourth primary aperture 111 are arrayed sequentially in a counter-clockwise direction about the primary button 110.

In some embodiments, the method further comprises inserting the secondary button 120 through a hole in a bone or tissue of a patient, as described herein, and tightening the sutures such that the primary button 110 and the secondary button 120 are tightly pressed against respective surfaces of the bone or tissue. In some embodiments, the tightening is performed by hand. In some embodiments, the tightening is performed by the lock driver as described herein. In some embodiments, the tightening is performed by the tightening tool as described herein.

In some embodiments, once the desired tension is reached, the lock 140 is tightened against the primary button 110 such that the sutures are locked in place therebetween. In some embodiments, the method further comprises trimming the loose ends of the sutures.

Method of Assembling A Suture Button Assembly

Provided herein, per FIGS. 23-26B are methods for assembling a suture button assembly 200. In some embodiments, the method comprises inserting the primary button 110 of a first suture button system 100 into a first insertion plate aperture 151 of the insertion plate 150, and inserting the primary button 110 of a second suture button system 100 into a second insertion plate aperture 151 of the insertion plate 150. In some embodiments, the method comprises inserting the secondary button 120 of a first suture button system 100 into a first insertion plate aperture 151 of the insertion plate 150, and inserting the secondary button 120 of a second suture button system 100 into a second insertion plate aperture 151 of the insertion plate 150. In some embodiments, the method comprises inserting the primary button 110 of a first suture button system 100 into a first insertion plate aperture 151 of the insertion plate 150, and inserting the secondary button 120 of a second suture button system 100 into a second insertion plate aperture 151 of the insertion plate 150.

In some embodiments, the method comprises inserting each of a plurality of suture strands 130 through one or more of the secondary apertures 121 of the secondary button 120 of a first suture button system 100, inserting each of a plurality of suture strands 130 through one or more of the secondary apertures 121 of the secondary button 120 of a second suture button system 100, inserting each of a plurality of suture strands 130 of the first suture button system 100 through a first insertion plate aperture 151 of the insertion plate 150, inserting each of a plurality of suture strands 130 of the second suture button system 100 through a second insertion plate aperture 151 of the insertion plate 150, inserting each of a plurality of suture strands 130 through one or more of the primary apertures 111 of the primary button 110 of a first suture button system 100, and inserting each of a plurality of suture strands 130 through one or more of the primary apertures 111 of the primary button 110 of a second suture button system 100.

In some embodiments, the method further comprises inserting the insertion screw 160 into the insertion hole 152 of the insertion plate 150. In some embodiments, the method further comprises screwing the insertion screw 160 into a bone or tissue of a patient. In some embodiments, screwing the insertion screw 160 into a bone or tissue of a patient temporarily fixates the plate to the bone or tissue of the patient while the suture-button system is deployed.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the term "generally" refers to a geometric relationship between two or more elements within tolerances of 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

EXAMPLES

The following illustrative examples are representative of embodiments of the systems, and methods described herein and are not meant to be limiting in any way.

Example 1

Syndesmosis Repair

In one example of an ankle syndesmosis repair, suture-button assembly is used, wherein the secondary button rests on the tibia and the primary button rests on the fibula. The plate of the suture-button assembly is placed on the fibula across a fracture, so that one suture-button system is deployed on either side of the fracture. The insertion screw is used to temporarily fixate the plate to the fibula while the suture-button system is deployed.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A suture-button system comprising:
   (a) a suture strand;

(b) a primary button having a primary aperture and a primary threaded portion, the primary aperture configured to receive the suture strand therethrough;

(c) a secondary button having a secondary aperture configured to receive the suture strand therethrough, such that the suture-button system is configured to clamp at least one targeted tissue of a subject between a distal surface of the primary button and a proximal surface of the secondary button upon applying a tension to the suture strand;

(d) a lock having a secondary threaded portion, wherein the secondary threaded portion is configured to be removably coupled to the primary threaded portion, wherein coupling the secondary threaded portion of the lock to the primary threaded portion secures the at least one targeted tissue clamped between the primary button and the secondary button, the lock further comprising a driver feature, an alignment feature, or both; and (e) a tensioning system having a tensioning feature configured to i) rotate the driver feature or couple to the alignment feature, ii) apply tension to the suture strand, or both
wherein the tensioning system comprises
(a) a handle rod having the tensioning feature at a distal portion thereof the tensioning feature configured to rotate the driver feature of the lock;
(b) a threaded rod configured to be coupled to a threaded feature within a channel of the handle rod;
(c) a knob coupled to a proximal end of the threaded rod, the knob located proximal to the handle rod; and
(d) a spinner disposed between the knob and the handle rod, wherein the spinner comprises i) an aperture accepting the threaded rod, and ii) a terminator channel configured to accept an end of the suture strand.

2. The system of claim 1, wherein the knob is coupled to the proximal end of the threaded rod by a pin, an adhesive, a fastener, a press-fit, a weld, or any combination thereof.

3. The system of claim 1, wherein the spinner rotates freely about the threaded rod, the knob, or both.

4. The system of claim 1, wherein rotating the knob and the threaded rod in a first direction with respect with to the handle rod translates the spinner proximally from the handle rod, thereby applying tension to the suture strand.

5. The system of claim 1, wherein rotating the handle rod in a first direction inserts the secondary threaded portion of the lock distally through the primary threaded portion.

6. The system of claim 1, wherein the primary button comprises at least 4 primary apertures.

7. The system of claim 1, wherein the lock comprises a head and wherein the secondary threaded portion extends from the head.

8. The system of claim 7, wherein a distal surface of the head is tapered outwards from a center axis of the lock.

9. A suture-button system comprising:
(a) a plurality of sub-systems, each sub-system comprising:
(i) a suture strand;
(ii) a primary button having a primary aperture configured to receive the suture strand therethrough;
(iii) a secondary button having a secondary aperture configured to receive the suture strand therethrough, such that the suture-button system is configured to clamp at least one targeted tissue of a subject between a distal surface of the primary button and a proximal surface of the secondary button upon applying a tension to the suture strand; and (iv) a lock, wherein the lock is configured to be removably coupled to the primary button, wherein coupling the lock to the primary button secures the at least one targeted tissue clamped between the primary button and the secondary button, the lock further comprising a driver feature, an alignment feature, or both;

(b) an insertion plate comprising a plurality of insertion plate apertures, wherein each insertion plate aperture is configured to receive i) the primary button of a sub-system of the plurality of sub-systems, or ii) the secondary button of a sub-system of the plurality of sub-systems;

(c) an insertion screw configured to be removably coupled to a screw hole disposed through the insertion plate; and (d) a tensioning system having a tensioning feature configured to i) rotate the driver feature or couple to the alignment feature, ii) apply tension to the suture strand, or both
wherein the tensioning system comprises
(a) a handle rod having the tensioning feature at a distal portion thereof, the tensioning feature configured to rotate the driver feature of the lock;
(b) a threaded rod configured to be coupled to a threaded feature within a channel of the handle rod;
(c) a knob coupled to a proximal end of the threaded rod, the knob located proximal to the handle rod; and
(d) a spinner disposed between the knob and the handle rod, wherein the spinner comprises i) an aperture accepting the threaded rod, and ii) a terminator channel configured to accept an end of the suture strand.

10. The suture-button system of claim 9, wherein each sub-system further comprises:
(a) a primary threaded portion located within the primary button; and
(b) a secondary threaded portion located on the lock, wherein the secondary threaded portion is configured to be removably coupled to the primary threaded portion, wherein coupling the secondary threaded portion of the lock to the threaded portion secures the clamping of the at least one targeted tissue.

11. The assembly of claim 10, wherein the lock comprises a head and wherein the secondary threaded portion extends from the head.

12. The assembly of claim 11, wherein a distal surface of the head is tapered outwards from a center axis of the lock.

13. The assembly of claim 9, wherein the screw hole is positioned between two of the plurality of insertion plate apertures.

14. The assembly of claim 13, wherein the screw hole is positioned equidistant between the two of the plurality of insertion plate apertures.

15. The assembly of claim 9, wherein the insertion screw comprises a first portion having a dimension greater than a dimension of the screw hole, and a second portion configured to attach to a bone of a patient.

16. The assembly of claim 15, wherein the first portion of the insertion screw prevents a proximal end of the insertion screw from passing through screw hole.

17. The assembly of claim 15, wherein the second portion comprises a threaded feature.

18. The assembly of claim 9, wherein a sub-system of the plurality sub-system has the primary button having at least 4 primary apertures.

\* \* \* \* \*